US011802881B2

(12) United States Patent
Manneh et al.

(10) Patent No.: US 11,802,881 B2
(45) Date of Patent: Oct. 31, 2023

(54) SATURATION BINDING RATIOMETRIC ASSAY

(71) Applicant: LumiraDx UK Ltd., London (GB)

(72) Inventors: Victor Manneh, Encinitas, CA (US); Sergei Svarovsky, San Diego, CA (US)

(73) Assignee: LumiraDx UK Ltd., London (GB)

( * ) Notice: Subject to any disclaimer, the term of this patent is extended or adjusted under 35 U.S.C. 154(b) by 0 days.

(21) Appl. No.: 17/409,279

(22) Filed: Aug. 23, 2021

(65) Prior Publication Data

US 2021/0382075 A1 Dec. 9, 2021

Related U.S. Application Data

(63) Continuation of application No. 16/293,628, filed on Mar. 5, 2019, now abandoned.

(51) Int. Cl.
*G01N 33/72* (2006.01)
*G01N 33/543* (2006.01)

(52) U.S. Cl.
CPC ......... *G01N 33/723* (2013.01); *G01N 33/543* (2013.01); *G01N 33/54326* (2013.01); *G01N 2333/805* (2013.01)

(58) Field of Classification Search
CPC ............. G01N 2333/805; G01N 33/49; G01N 33/543; G01N 33/54326; G01N 33/72; G01N 33/721; G01N 33/723; Y10T 436/255
USPC ..... 436/63, 66, 67, 149, 150, 151, 164, 172, 436/178, 526; 435/7.1
See application file for complete search history.

(56) References Cited

U.S. PATENT DOCUMENTS

| 4,269,605 A | 5/1981 | Dean et al. |
| 4,647,654 A * | 3/1987 | Knowles ............... C07K 16/18 530/812 |
| 4,861,728 A | 8/1989 | Wagner |
| 5,110,745 A | 5/1992 | Kricka et al. |
| 5,206,144 A * | 4/1993 | Zeuthen ............... C07K 16/18 435/7.25 |
| 5,284,777 A | 2/1994 | Rosenthal et al. |
| 5,932,480 A | 8/1999 | Maruo et al. |

(Continued)

FOREIGN PATENT DOCUMENTS

| EP | 0316306 A2 | 5/1989 |
| WO | WO-96/03657 A1 | 2/1996 |

(Continued)

OTHER PUBLICATIONS

Dandliker et al. Fluorescence polarization immunoassay. Theory and experimental method. J. Immunochemistry 10, 219-227 (1973).

(Continued)

*Primary Examiner* — Maureen Wallenhorst
(74) *Attorney, Agent, or Firm* — Goodwin Procter LLP

(57) ABSTRACT

Methods, devices, and reagents are described for performing ratiometric assays for hemoglobin A1c. The methods involve a direct ratio determination between Hb A1c and normalized total hemoglobin utilizing a saturating amount of hemoglobin so that Hb A1c binds proportionately to a substrate. In some applications, the assay utilizes a proximity label system for signal generation and/or labeled magnetic beads. The methods can be configured as homogeneous or heterogeneous assays.

15 Claims, 9 Drawing Sheets

Specification includes a Sequence Listing.

(56) References Cited

U.S. PATENT DOCUMENTS

| | | | |
|---|---|---|---|
| 6,174,734 B1* | 1/2001 | Ito | G01N 33/723 435/7.1 |
| 6,406,913 B1 | 6/2002 | Ullman et al. | |
| 8,557,590 B2* | 10/2013 | Bae | G01N 33/723 436/523 |
| 9,459,262 B2* | 10/2016 | Rutter | G01N 33/721 |
| 9,624,522 B2 | 4/2017 | Gaustad et al. | |
| 2011/0117670 A1 | 5/2011 | Walker et al. | |
| 2012/0149128 A1 | 6/2012 | Manneh | |
| 2015/0316541 A1* | 11/2015 | Tetsu | G01N 33/5306 435/7.1 |
| 2016/0320415 A1 | 11/2016 | Manneh | |
| 2017/0176462 A1* | 6/2017 | Walker | G01N 33/723 |
| 2017/0176463 A1* | 6/2017 | Manneh | G01N 33/582 |
| 2019/0137522 A1* | 5/2019 | Manneh | G01N 33/54306 |

FOREIGN PATENT DOCUMENTS

| | | |
|---|---|---|
| WO | WO-98/40750 A1 | 9/1998 |
| WO | WO-2013059293 A1 | 4/2013 |

OTHER PUBLICATIONS

Dandliker et al. Quantification of the antigen-antibody reaction by the polarization of fluorescence. Biochem. Biophys. Res. Commun. 5, 299 (1961).

Devlin et al. Homogeneous detection of nucleic acids by transient-state polarized fluorescence. Clinical Chemistry 39, 1939-1943 (erratum 2343), (1993).

Eissa et al. "Aptamer-Based Label-Free Electrochemical Biosensor Array for the Detection of Total and Glycated Hemoglobin in Human Whole Blood," Scientific Reports, Apr. 21, 2017, vol. 7, No. 1016, pp. 1-8.

Engel & Khanna, CEDIA in In vitro diagnostics with a novel homogeneous assay technique. Current Status and future prospects, J Immunol Methods, 1992, 150(1-2):99-102.

Guo et al. Use of a long-lifetime Re(I) complex in fluorescence polarization immunoassays of high molecular weight analytes. Anal. Chem. 70, 632-637 (1998).

Henderson et al, CEDIA, a new homogeneous immunoassay system, Clin Chem, 1986, 32(9): 1637-41.

Litman et al. Enzyme channeling immunoassay: a new homogeneous enzyme immunoassay technique. Anal. Biochem. 106, 223-229 (1980).

Ullman et al. Homogeneous immunoassays and immunometric assays. In Diagnostic Immunology: Technology Assessment and Quality Assurance. Eds. Rippey, J.H. & Nakamura, R.M., 31-46 (College of American Pathologists, Skokie, IL, 1984).

Ullman et al. 1996, Clin Chem 42(9): 1518-26.

Extended European Search Report for EP Patent Application No. 3934683, dated Apr. 14, 2023, 8 pages. Ullman et al. (1994) *Proc. Natl. Acad. Sci. USA* 91:5426-5430.

Ullman, Edwin F., et al. "Luminescent oxygen channeling immunoassay: measurement of particle binding kinetics by chemiluminescence." Proceedings of the National Academy of Sciences, 91(12): 5426-5430.

* cited by examiner

Fig. 4
Assay response to commercial A1c calibrators
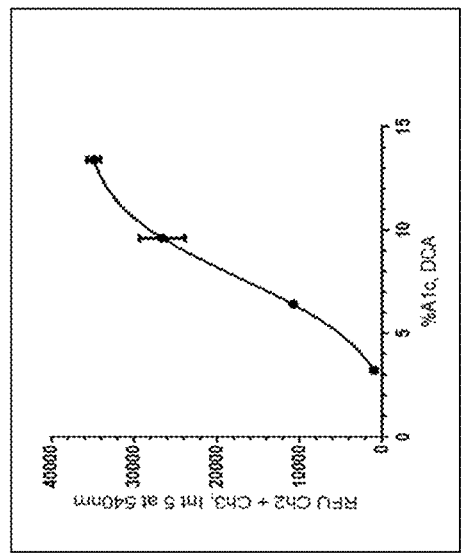
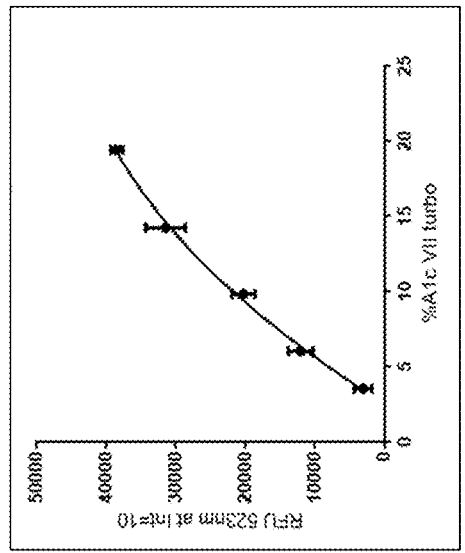

Response to synthetic A1c calibrators

SATURATION BINDING RATIOMETRIC ASSAY

RELATED APPLICATIONS

This application is a continuation of U.S. patent application Ser. No. 16/293,628, filed on Mar. 5, 2019, now abandoned, which is incorporated by reference herein in its entirety.

FIELD OF THE INVENTION

The present invention relates to an assay for glycated hemoglobin.

SEQUENCE LISTING

The sequence listing submitted herewith as ASCII text file entitled XENB2204_SeqListing_ST25.txt, created on Mar. 3, 2019, with a size of 1690 byte, is incorporated herein by reference in its entirety.

BACKGROUND OF THE INVENTION

The following discussion is provided solely to assist the understanding of the reader, and does not constitute an admission any of the information discussed or references cited constitute prior art to the present invention.

Control of blood glucose concentrations in diabetic patients has been shown to decrease the frequency and severity of long-term microvascular and neurologic complications of the disease. It has been found that the rate of formation of glycated hemoglobin is directly related to the glucose concentration in blood. As a result, in the management of glucose levels, measurement of glycated hemoglobin is used to determine how well blood glucose concentration has been managed over extended time periods.

Typically, the average lifetime for red blood cells is about 120 days. Therefore, determination of the percent glycation of hemoglobin correlates with the average glucose concentration during that period of time, and especially over the previous 2-3 months. Therefore, the percent glycated hemoglobin is an indicator of glycemic control over that time period.

Some methods to determine the concentration or percent of glycated proteins have utilized dihydroxyboryl compounds which bind to the 1,2 cis diols of the carbohydrate of glycated proteins to separate them from non-glycated proteins. Such methods include those described in U.S. Pat. Nos. 4,269,605, 5,284,777, 5,110,745, 4,861,728, PCT Appl. WO 96/03657), and PCT application WO 9840750.

A Hb A1c assay which uses non-specific adsorption of blood components, including hemoglobin, to a solid phase simultaneously with contacting the hemoglobin with anti-A1c antibody, followed by detection of bound Hb A1c is described in Maruo, U.S. Pat. No. 5,932,480. The method involves a pre-treatment step under denaturing conditions prior to binding the hemoglobin on the solid phase. The non-specific adsorption used in Maruo has the drawback that such adsorption is subject to many interferences and requires a substantial wash step to remove unbound A1c before adding the anti-A1c. Such wash step commonly results in greater imprecision. In contrast, the present invention can be performed with specific-binding reagents which have much higher affinity for A1c in the bound than in the un-bound state, eliminating the necessity for the wash step to remove unbound A1c before contacting with anti-A1c. In addition, use of specific total hemoglobin binding modality affords elimination of cross reactivity with undesirable isoforms of hemoglobin, such as HbF, that are deleterious for accurate measurement of percent A1c, technically defined as the percent of glycated HbA isoform of hemoglobin.

SUMMARY OF THE INVENTION

This invention is directed to assays and corresponding devices and reagents for ratiometric assays of glycated hemoglobin (generally referred to as Hb A1c). As is generally understood, detection of glycated hemoglobin is useful in the management of blood glucose levels in diabetic patients and for monitoring the status of pre-diabetic individuals. Assays are described herein which provide rapid, high precision assays amenable to use in a variety of settings, including in point-of-care settings.

The present assays effectively eliminate a significant source of imprecision in current assays by normalizing one of the principal measurements normally used in determination of the analyte ratio in the hemoglobin A1c ratiometric assay. This is accomplished by selecting consistently prepared surfaces, e.g., beads, for binding hemoglobin. When bound to saturation on the surface, the amount of hemoglobin bound on each bead (or per unit surface area) is then essentially constant, and can be treated as actually constant when averaged over a large number of beads (or large number of surface area units). The result of effectively normalizing the amount of hemoglobin bound per unit surface area (e.g., per bead for monodisperse beads) is that measurement of the signal level from the A1c subpopulation of the hemoglobin immediately provides the fraction of hemoglobin which is represented by the A1c subpopulation. In addition, the present assays are simpler to run than conventional ratiometric assays, in many applications allowing simplification of assay cartridges or other assay devices.

Thus, a first aspect of the invention concerns a method for determining the fraction (e.g., percent) of hemoglobin A1c in the total population of hemoglobin and/or as compared to the population of hemoglobin excluding the A1c sub-population. The A1c subpopulation(s) can be measured directly, often without directly measuring the total hemoglobin population. That is, the assay can determine the fraction of glycated hemoglobin (e.g., fraction Hb A1c) compared to the total Hb directly by measuring the signal from Hb A1c only, without directly measuring the total hemoglobin.

The method involves contacting a surface (e.g., beads or other particles, or well or lateral flow strip surface) bearing first specific binding agent (e.g., antibody) binding total hemoglobin with a sample containing an excess of hemoglobin which may include Hb A1c, thereby saturating binding of total hemoglobin on the surface, contacting the sample or bound hemoglobin with an excess of labeled second binding agent specific for A1c (an excess sufficient to bind to all or substantially all of the bound A1c), determining a signal from the labeled second binding agent bound to Hb A1c bound on said particles, where the signal from the labeled second binding agent bound to Hb A1c on the particles is indicative of the fraction of total hemoglobin which is Hb A1c.

In advantageous embodiments, the first specific binding agent, e.g., anti-Hb antibody, is selected such that binding of Hb to the first specific binding agent exposes the amino-terminal peptides of the beta-chain (including A1c moieties) in a manner which facilitates binding of anti-A1c to the Hb.

In illustrative embodiments, the method involves contacting particles bearing anti-hemoglobin antibody (anti-Hb Ab)

with a sample containing an excess of hemoglobin resulting in saturation binding of hemoglobin to the particles in the range desired such as 3-30 g/dl or more often 4-20 g/dl, contacting hemoglobin in the sample or hemoglobin bound on the particles with an excess of labeled anti-A1c binding agent (e.g., anti-A1c Ab), measuring a signal from the portion of the labeled anti-A1c binding agent bound to A1c on the particles, where the signal from the labeled anti-A1c binding agent is directly indicative of the fraction of hemoglobin in the sample which is hemoglobin A1c, without having to measure each component alone and then calculate the percent A1c from the separate measurements.

In some highly advantageous embodiments, the anti-Hb Ab binds to an epitope, and/or is obtained using immunization with an immunogen containing a short peptide comprising a 5, 6, 7, 8, 9, or 10 amino acid sequence from the indicated sequence region and isolation and selection of resulting antibodies having the indicated binding activity, located near the amino terminal end of the Hb beta subunit, typically within amino acids 3-30 or 7-25 inclusive, e.g., within amino acids 3-8, 7-11, 7-12, 7-13, 8-12, 8-13, 9-13, 14-18, 19-23, 24-28, 3-12, 7-14, 7-15, 7-16, 7-18, 8-14, 8-15, 8-18, 9-15, 9-18, 14-23, 19-28, 21-30, 3-16, 7-20, 8-20, 9-22, 14-27, 17-30, 3-18, 7-22, 8-23, 9-24, 13-28, 3-20, 7-24, 8-25, 9-26, 13-30, 3-22, 7-25, 7-26, 8-27, 9-28, 11-30, 3-27, 7-30, or 3-30, selected such that binding of the Hb antibody does not interfere with binding of the selected anti-Hb A1c antibody, e.g., does not interfere with binding of an anti-Hb A1c antibody having a $dF^1VH^2$ binding epitope, preferably binding of such anti-Hb antibody exposes the A1c epitope, thereby making it available for binding with anti-A1c. In advantageous embodiments using an anti-Hb antibody as just specified, the anti-A1c binding agent binds with A1c bound with the anti-total Hb sufficiently for an effective assay even in the presence of an at least 10, 50, 100, 150, 200, 250, or 300-fold excess of unbound Hb A1c as compared to the number of anti-A1c binding agent. In such embodiments, the assay may be performed with the binding of total Hb to first surface (e.g., first particles such as beads) at the same time the first surface is contacted with anti-A1c or the contacting with anti-A1c may be performed after total Hb is bound to first surface.

In some embodiments, a sandwich is formed comprising a first particle and labeled second specific binding agent. A first particle is a magnetic particle (bead) which binds total hemoglobin, including the Hb A1c sub-population. Advantageously, the first particle can be dyed (e.g., with an absorption, fluorescent, quantum dot or TRF dye). The total hemoglobin (e.g., in a diluted or non-diluted blood sample) is contacted with first particles under conditions such that total hemoglobin saturation binds on first particles. A label, often in the form of a labeled second particle, is directly or indirectly linked with second specific binding member which specifically binds with the A1c subpopulation. The total hemoglobin is contacted with the label, e.g., labeled second particles, which specifically binds with the A1c subpopulation of the total hemoglobin.

In particular embodiments, the order and timing of the contacting can be done in several different ways. In certain embodiments, the contacting may be performed sequentially, e.g., total hemoglobin contacted with first particles followed by contacting total hemoglobin with second particles or other labeled second specific binding agent, either before or after separating first particles or other surface bearing first specific binding agent from unbound total hemoglobin. In either case, an excess of second particles or other labeled second specific binding agent should be used to ensure substantially all of the A1c subpopulation, or at least substantially all of the bound A1c subpopulation, present binds with second particles or other labeled second specific binding agent. Alternatively, total hemoglobin can be contacted with an excess of second particles or other labeled second specific binding agent, followed by contacting total hemoglobin with first particles. In other alternatives, the contacting of total hemoglobin with first particles and an excess of second particles or other labeled second specific binding agent may be carried out substantially simultaneously.

In some embodiments, the first particles are magnetic beads (which may be labeled with a detectable label such as absorbance, colorimetric, fluorescent, quantum dot, or TRF label) bearing anti-Hb first binding agent which is selected such that binding of Hb to the first binding agent causes the amino terminal end of the Hb beta chain to become exposed. The result of this anti-Hb selection is that anti-A1c preferentially binds with bound Hb rather than free Hb, where the differential in binding may, for example, be at least 10, 20, 50, 100, 200, 500, 1000, 1500, or 2000-fold. The Hb binds to saturation on the first particles. The bound Hb, with its exposed amino terminal amino acids, is contacted with anti-A1c second binding agent. Advantageously, anti-A1c is chosen which preferentially binds with Hb A1c which is bound with anti-Hb rather than to free Hb A1c. This choice of anti-A1c allows a reduced quantity of anti-A1c to be used because the free Hb A1c does not substantially compete for binding with the bound Hb A1c. The anti-A1c is or becomes directly or indirectly linked with a detectable label. Thus, in some cases, the anti-A1c is linked with a labeled second particle bearing anti-A1c when it binds with the bound Hb. In other cases, the anti-A1c is linked with an third specific binding agent which is part of a specific binding pair, e.g., one of biotin or streptavidin, forming a conjugate, and the labeled second particle bears the other part of the specific binding pair and binds with the anti-A1c conjugate. In still other cases, the second specific binding agent is recognized and binds directly by a third specific binding agent e.g., an anti-second specific binding agent such as an antibody, linked with a detectable label. The detectable label (e.g., labeled second particles), are then separated, e.g., washed away, from the bound HB-anti-A1c-label complexes, and the signal from the complexes is detected as a measure of the fraction, e.g., percentage, of A1c in the sample. In some embodiments, assay reagents, e.g., lysis reagents, Hb-binding reagents, and/or A1c-binding reagents are in dry form prior to contact with sample solution, e.g., in the form of fast reconstituting reagent pellets.

In certain embodiments in which the first particles are magnetic beads, the assay is conducted in an assay cartridge, and the sample may be contacted with lysing agent, e.g., lysing detergents and/or lytic peptides such as those mentioned herein, either before introducing the sample into the cartridge or within an initial portion of the cartridge or in the same area (e.g., zone) as binding of Hb with anti-Hb and/or binding of anti-A1c with bound Hb. In advantageous cases, lysis reagent(s) is/are in dry form, e.g., as fast reconstituting reagent pellets, and reconstitute upon contact with the sample solution. The lysed sample is moved to a channel or strip, which may have one zone or multiple zones, e.g., 2, 3, 4, 5, 6, or even more zones where different steps of the assay are carried out in different zones. In certain cases, all steps after lysing are carried out in one zone, i.e., sample contacts anti-Hb magnetic particles, e.g, beads, which may be detectably labeled. Advantageously the anti-Hb can be chosen to expose the amino terminal amino acids of the Hb beta chain upon binding. The sample is also contacted with labeled anti-A1c, e.g., labeled beads which bear anti-A1c. Advantageously, anti-A1c is chosen which preferentially binds with Hb A1c which is bound with anti-Hb rather than to free Hb A1c. After binding of anti-A1c to the Hb A1c fraction of the bound Hb, the magnetic beads are immobilized with a magnet, and the unbound anti-A1c label is washed away. The signal from the bound anti-A1c label is then read as a measure of the fraction of Hb A1c in the Hb sample. If desired, signal from labeled anti-Hb beads can be read to provide a normalizing determination of the number of anti-Hb beads present, which is also a normalizing indication of the amount of Hb bound to the magnetic beads at saturation. In other cases, multiple zones are used. For example, the lysed sample can be moved to a first zone where the sample contacts magnetic anti-Hb beads and saturation binding occurs. The solution containing Hb bound to anti-Hb beads is moved to a second zone in which the sample contacts labeled anti-A1c such that anti-A1c binds to Hb A1c bound on the anti-Hb magnetic beads. The magnetic beads are immobilized using a magnet, the unbound labeled anti-A1c is washed away, and the signal from the label linked with the anti-A1c in the magnetic bead/anti-Hb/Hb/anti-A1c-label complexes is read as a measure of the fraction of Hb A1c in the sample. If the magnetic beads are detectably labeled, the signal from those beads can also be read as a normalizing measure of the number of magnetic beads present, which is also a normalizing measure of the amount of Hb bound at saturation.

In some embodiments, the hemoglobin binding capacity of the first particles is pre-determined and is substantially constant so a known quantity of first particles has a known hemoglobin binding capacity and the average signal from a first particle is a constant.

Alternatively, the first particles may be labeled, e.g., with a fluorescent label, quantum dot, TRF, or colorimetric label, which can be read separately from label specifically bound to A1c. The average signal from each first particle is a constant, so the total signal emitted from a set of first particles is proportional to the number of first particles being read (or can be correlated with a standard curve). The number of first particles being read thus provides a normalizing surrogate for the amount of total hemoglobin bound at saturation to the first particles.

In certain embodiments, sample is contacted with labeled second binding agent specific for A1c before or essentially simultaneously with contacting sample with particles bearing anti-total hemoglobin binding agent. In other embodiments, the sample is first contacted with particles bearing anti-hemoglobin binding agent, then contacted with labeled second binding agent specific for A1c. In certain further embodiments, unbound labeled second binding agent specific for A1c is separated from bound labeled second binding agent specific for A1c prior to reading signal from bound labeled second binding agent specified for A1c.

In some embodiments, the method includes lysing cells to release the hemoglobin and/or at least partially denaturing the hemoglobin, e.g., using lysing detergents and/or lytic pepetides such as those indicated herein.

In some embodiments, the method also includes detection and/or quantitation of the presence of one or more hemoglobin isoforms, e.g., isoforms S, C. E., D, and/or F. These embodiments require, of course, specific binding agents, e.g., antibodies, for the respective isoform(s).

In certain embodiments, signal(s) corresponding to the hemoglobin, A1c, and/or isoform variants (e.g., hemoglobin isoforms S, C, E, D, and/or F) is/are fluorescence signals, Time Resolve Fluorescence (TRF) signals or phosphorescence signals, luminescence signals, chemiluminescence signals, colorimetric signals, absorbance signals, and/or resonance light scattering signals; (the hemoglobin bind to magnetic beads, the anti-A1c, e.g., anti-A1c-TRF or fluorescence labeled anti-A1c, will bind to the hemoglobin bound to magnetic bead, this will calculate the percent A1c in the hemoglobin) the detecting is performed on a lateral flow assay device, where the device includes a detection zone with an immobilization site for total hemoglobin.

In some embodiments incorporating magnetic beads as first particles, the magnetic particles are contacted with sample and with second specific binding agent in a chamber within an assay cartridge and signal is read in the same chamber after removal of unbound second specific binding agent; the magnetic beads are contacted with second specific binding agent in a chamber within an assay cartridge and signal is read in the same chamber; after contact with sample and second specific binding agent the magnetic beads are moved to a different chamber in which signal is read. In certain embodiments, the assay is performed as a heterogeneous assay or as a homogeneous assay; the assay method utilized a Luminescent Oxygen Channeling assay (LOCI) signal, FRET assay signal, TR-FRET assay signal, FP assay signal, EMIT assay signal, enzyme channeling assay signal, and/or CEDIA assay signal.

In certain embodiments, the assay incorporates Luminescent Oxygen Channeling assay (LOCI) labels which include donor and acceptor labels. In particular embodiments using LOCI, the assay is performed as a homogeneous assay or the assay is performed as a quasigenous (or exchange immunoassay) assay. The total hemoglobin will saturate the first bead (e.g., acceptor bead), the anti-A1c conjugated or linked (which may be accomplished in situ) to the donor bead will bind to A1c in the hemoglobin on the acceptor bead, forming a donor-A1c-acceptor sandwich. The energy transfer signal (LOCI signal) is then a measure of fraction (e.g., percent) glycation of the hemoglobin, i.e., fraction A1c.

In certain embodiments, the first particle is a magnetic bead which bears anti-Hb, In certain embodiments, the coefficient of variation of the calculated Hb A1c for sample levels within the effective range of the assay system (e.g., 2-14, 4-14, 2-20, or 2-14 g/dL A1c) is less than 3.0, 2.7, 2.5, 2.3, 2.1, 2.0, 1.9, 1.8, 1.7, 1.6, 1.5, 1.4, 1.3, or 1.2%, based on a minimum of 20 replicate measurements.

For advantageous embodiments, the hemoglobin-containing sample is undiluted blood (excluding dilution occurring from reagent reconstitution and/or liquid reaction reagent addition, e.g., cell lysis solution); the assay is performed without hemoglobin denaturation; the assay is performed as a dry assay (i.e., all assay reagents are present in an assay device in dried form); the assay sample is applied to the assay device following cell lysis; cell lysis is performed in an assay device.

A related aspect concerns a method for determining the fraction of Hb A1c as a fraction of total Hb in a sample and/or as compared to the population of the Hb excluding the Hb A1c sub-population and/or compared to the fraction of one or more other Hb sub-populations (e.g., Hb isoform(s)) without directly measuring or requiring directly measuring the concentration of the total hemoglobin. For example, the assay can determine the fraction of Hb A1c compared to the total Hb or to the total Hb which is not glycated at the terminal valine of the beta chain directly (without measuring or requiring measuring the concentration of total hemoglobin. The method involves saturated binding of total Hb to beads followed by or concurrent with binding the A1c with labeled binding agent. The beads can be moved and/or held in a controlled fashion, e.g., using magnetic fields, electric fields, and/or fluid flow.

Thus, significant embodiments of this method involve contacting dyed (i.e., labeled) magnetic beads bearing first specific binding agent against total hemoglobin or using non-specific electrostatic binding (such that beads and hemoglobin have opposite net charges), with a sample containing an excess of the hemoglobin which may include an A1c subpopulation and/or hemoglobin isoforms, thereby saturating binding of total hemoglobin on the surface in the range desired, contacting the sample or hemoglobin bound on the magnetic beads with an excess of second labeled binding agent specific for A1c thereby forming a sandwich comprising magnetic bead, specifically bound total hemoglobin, and second labeled binding agent (e.g. anti-Hb A1c or phenylboronate TRF beads). In heterogeneous implementations, the sandwiches comprising magnetic beads are separated from unbound second labeled binding agent, e.g., by holding the magnetic beads with a magnetic field and removing unbound second labeled binding agent or by moving the magnetic beads to a reading zone separated from unbound second labeled binding agent using a magnetic field. A first signal is determined from the dyed magnetic beads, where the intensity of the first signal is a normalizing measure of the number of magnetic beads and therefore also a normalizing measure of the bound total hemoglobin. For example, to improve precision, where the number of magnetic beads determines the total hemoglobin bound at saturation, adding color to the magnetic beads and directly measuring the number of beads based on color present can be used to minimize variability due to particle dispensing and/or particle movement. A second signal is determined from the second labeled binding agent bound to A1c bound with the magnetic beads. The intensity of the second signal is a measure of the amount or the fraction of bound A1c (e.g. percent A1c). A ratio of A1c subpopulation to total hemoglobin can then be calculated from the respective measures of total number of particles saturated with bound hemoglobin and signal from A1c subpopulation.

In homogeneous implementations, e.g., homogeneous assays using LOCI, FRET, TR-FRET, or other proximity label system, signal is typically read without separating the unbound from bound second labeled binding agent. That is, binding of second labeled binding agent can enable the proximity label system to generate detectable signal, e.g., due to energy transfer as in FRET or singlet oxygen diffusion as in LOCI even in the presence of unbound second labeled binding agent.

In advantageous embodiments, a second specific binding agent is selected and used which preferentially binds with Hb A1c which is bound with anti-total hemoglobin rather than with free (i.e., unbound) Hb A1c. With such second specific binding agents, rather than using a wash step to remove unbound hemoglobin (including Hb A1c), this wash step may be omitted. In some highly advantageous embodiments, the first specific binding agent (most often anti-Hb Ab) binds to an epitope located near the amino terminal end of the Hb beta subunit, typically within amino acids 3-30 or 7-25 inclusive, e.g., within amino acids 3-8, 7-11, 7-12, 7-13, 8-12, 8-13, 9-13, 14-18, 19-23, 24-28, 3-12, 7-14, 7-15, 7-16, 7-18, 8-14, 8-15, 8-18, 9-15, 9-18, 14-23, 19-28, 20-30, 3-16, 7-20, 8-20, 9-22, 14-27, 17-30, 3-18, 7-22, 8-23, 9-24, 13-28, 3-20, 7-24, 8-25, 9-26, 13-30, 3-22, 7-25, 7-26, 8-27, 9-28, 11-30, 3-27, 7-30, or 3-30, selected such that binding of the Hb antibody does not interfere with binding of the selected anti-Hb A1c antibody, e.g., does not interfere with binding of an anti-Hb A1c antibody having a $dF^1VH^2$ binding epitope, preferably binding of such antibody exposes the A1c epitope, thereby making it available for binding with anti-A1c. In advantageous embodiments using an anti-Hb antibody as just specified, the anti-A1c binding agent binds with A1c bound with the anti-total Hb sufficiently for an effective assay even in the presence of a 10, 50, 100, 200-fold excess of unbound Hb A1c. In such embodiments, the assay may be performed with the binding of total Hb to first particles or beads at the same time the first particle or bead is contacted with anti-A1c or the contacting with anti-A1c may be performed after total Hb is bound to first particle or bead. In certain embodiments, the anti-A1c binds with bound Hb A1c at least 2, 5, 10, 20, 50, 100, 500, or 1000-fold greater than to free Hb A1c.

Rather than using magnetic beads, in some embodiments, separation of beads with saturated binding of total hemoglobin can be accomplished using charged beads and an electric field(s) to move or hold the beads, separating the beads from the labeled second specific binding agent.

Other beneficial embodiments, e.g., embodiments using magnetic beads incorporate the limitations specified for embodiments of the first aspect above.

Another related aspect concerns a single use assay kit comprising magnetic beads, which may be dyed or otherwise labeled, comprising first binding agent specific for total hemoglobin, and labeled second specific binding agent, where the second specific binding agent binds to the A1c subpopulation. Preferably the assay kit is a single use kit, such as a single use assay cartridge.

In particular embodiments, the assay kit contains a component or components as specified for embodiments of the assay methods above, assay reagents, such as lysing agent, the first hemoglobin specific binding agent, and/or the anti-A1c binding agent are provided in dry form in the assay kit (e.g., cartridge), for example as fast-reconstituting reagent pellets; reagent for lysis of red blood cells is provided in the assay kit, e.g., within an assay cartridge or in a separate container.

In some embodiments, the assay kit (e.g., assay cartridge) contains a first specific binding agent which binds within amino acid residues 3-30 or 7-25, or other sub-sequence as specified above, of beta chain of total hemoglobin (or with a sub-sequence thereof) and thereby exposes the A1c binding epitope of glycated hemoglobin beta chain, and a second specific binding agent (e.g., antibody) which binds with A1c. In certain embodiments which include specific binding agents, e.g., antibodies, as just indicated, the second binding agent is provided in a number amount less than the number amount of A1c in a blood sample volume for which the assay kit is designed, where, with reference to a blood sample which contains 14 g/dL hemoglobin of which 5.5% is Hb A1c, the A1c present is at least 10×, 20×, 50× 100×, 150×, 200×, or 250× excess over the number amount of Hb A1c from the blood sample which binds to first specific binding agent in the assay kit (e.g., assay cartridge) when hemoglobin from the sample is saturation bound with the first specific binding agent.

In certain embodiments, the first specific binding agent is linked with magnetic beads, which may be labeled, e.g., with light absorption dye, fluorescent label, quantum dot label, or TRF label; the assay kit comprises a cartridge having a chamber for immobilization of magnetic beads, said chamber may also be a chamber for reading signal from labeled second specific binding agent or there is a separate chamber in which signal from labeled second specific binding agent is read.

In some embodiments of an assay cartridge, the cartridge contains a channel with one or more zones in which assay steps are carried out. For example, the cartridge may have an optional first zone in which cell lysis is performed, followed by a second zone in which Hb in the sample binds with first specific binding agent (e.g., anti-Hb). Either in the same zone or in a third zone, second specific binding agent (e.g., anti-A1c) binds with bound Hb. Either in the same zone as the A1c to anti-A1c binding occurs or in a fourth zone, medium containing unbound Hb is displaced or washed away from bound Hb. The cartridge is configured such that signal from labeled second specific binding agent can then be detected in a zone, usually the same zone in which the displacement or wash occurs.

In particular embodiments, the first specific binding agent is linked with a proximity label donor or acceptor, and the second specific binding agent is directly or indirectly linked with a corresponding proximity label donor or acceptor, thereby constituting a donor/acceptor proximity label pair. For example the donor/acceptor pair may comprise a triplet oxygen generator and a chemiluminescent label which reacts with triplet oxygen and thereby generates a light emission, such as a LOCI label pair.

In certain embodiments, the assay device contains reagents as described for aspects above or otherwise described herein for use in the present methods.

Additional embodiments will be apparent from the Detailed Description and from the claims.

BRIEF DESCRIPTION OF THE DRAWINGS

FIG. 4 shows graphed assay results with commercial A1calibrators in a magnetic bead saturation A1c assay.

DETAILED DESCRIPTION OF THE PREFERRED EMBODIMENTS

Figure 1:
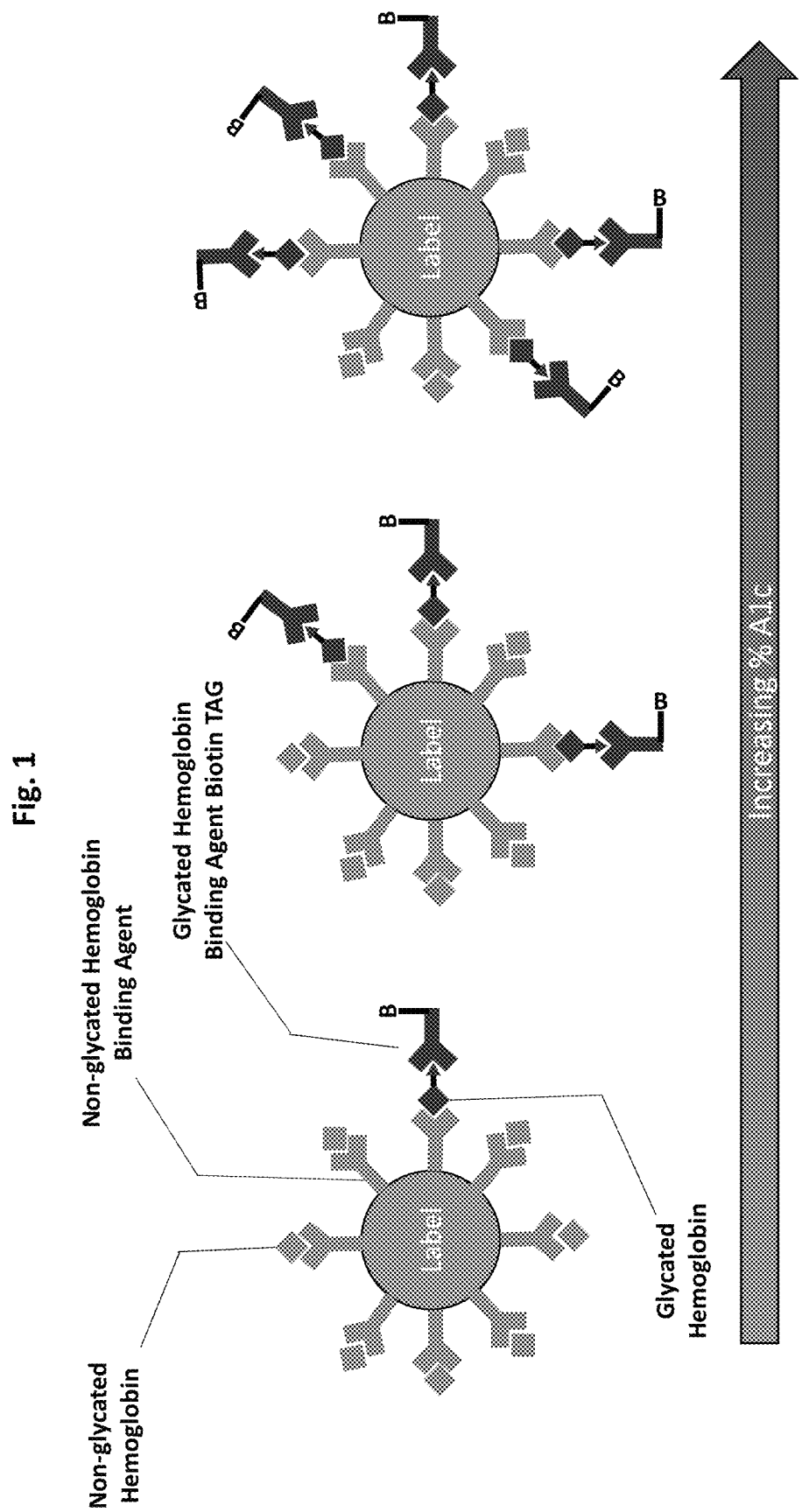
FIG. 1 schematically shows proportional specific binding of glycated hemoglobin to labeled bead for ratiometric saturated binding assay.

The present invention is directed to assay methods for detecting relative levels of particular sub-populations of hemoglobin, including Hb A1c. Detection of other Hb variants may also be included, such as detection of Hb isoforms. In some advantageous embodiments, the method uses a specific binding agent for total Hb which assists in exposing the A1c epitope for binding, e.g., binding with anti-A1c antibody. In such embodiments, the anti-A1c binding agent can advantageously be selected to preferentially bind with bound Hb A1c over unbound Hb A1c.

As indicated above, a method is provided for determining the fraction of Hb A1c in a sample as a fraction of the total population of hemoglobin and/or as compared to the population of hemoglobin excluding the Hb A1c population and/or compared to the fraction of one or more other particular sub-populations of the hemoglobin such as various Hb isoforms. Thus, for example, an assay can determine the fraction of glycated hemoglobin (e.g., Hb A1c) compared to the total Hb or to the total Hb which is not glycated at the terminal valine of the beta chain directly without measuring each fraction and determining the percent.

Most current ratiometric assays for Hb A1c use measurement of the levels of both total Hb and the A1c variant. The calculated ratio of the two measurements then provides the fraction of total Hb which is Hb A1c. As a result, such assays are subject to variability in two independent measurements, which degrades achievable assay precision.

In contrast, the present methods effectively normalize the total Hb amount and therefore involves only one variable measurement, i.e., measurement of the A1c subpopulation. These methods are based on using saturation binding of total hemoglobin on a particle (e.g., bead), plate well, or other surface. For example, as illustrated by Hb A1c, the method can be based on saturation binding of total Hb on particles. The hemoglobin bound to the particle or other surface will have each Hb variant proportionally represented in the bound hemoglobin population, but the total quantity of Hb bound to each particle will be essentially constant. As a result, the quantity of total hemoglobin bound to a fixed number of particles will be essentially constant. Therefore, all that is needed is to quantify the number of particles used in the assay, i.e., the number of particles detected. Essentially, the determination of total hemoglobin is replaced by the number of particles, which can, if desired, be made a constant in the assay. The fraction of the A1c sub-population is then provided by the signal obtained from labeled binding agent which specifically binds to the A1c sub-population.

If desired, the number of particles can be variable and the number of particles is determined by the signal from the particles. That is, labeled particles are used, e.g., fluorescent labeled, quantum dot, TRF, or colored polystyrene particles. By using particles which are uniform in size and are uniformly labeled, the label on each particle is essentially constant, and therefore the signal from each particle is essentially constant. As a result, the intensity of the label signal directly indicates the number of labeled particles present, which then correlates directly with the total hemoglobin binding capacity.

These Hb A1c detection methods are useful, for example, for monitoring the average levels of blood glucose in an individual (usually human, but the methods are also applicable to other animals, particularly other mammals). While numerous methods are available for determining glucose levels at a particular time point, it is also important to be able to monitor average levels over time. It has been found that the glycation levels of hemoglobin correlates strongly with average glucose levels over a preceding time period corresponding to the average lifetime of Hb protein molecules in the body. Because of the approximate 120 day lifetime of hemoglobin in the blood, glycated hemoglobin is useful as an indicator of average glucose levels over the preceding 2-3 months, with greater weighting on the prior one month. Thus, the present methods may be used to quantitate relative levels of glycated hemoglobin.

A. General Assay Approach

As indicated above, in the present methods and assays the ratio of Hb A1c to total hemoglobin (or to total hemoglobin minus the A1c subpopulation) is used. There are also existing Hb A1c assays which determine the relative levels of A1c in a population of Hb in which only some of the Hb complexes are glycated to the A1c form. These existing assays generally determine a level of Hb A1c and a level of total Hb (or just the respective signal levels), and then calculate the proportion of A1c in the sample. With appropriate selection of label system, the assay methods may be configured as either homogeneous (typically using a proximity label system) or heterogeneous assays.

In contrast, the present assays measure the percent of Hb A1c directly using saturation binding of the total hemoglobin population in the target concentration range. In many cases, the A1c subpopulation fraction is determined without direct determination of total target hemoglobin, e.g., by reference to a standard curve or by determination of the number of particles present. Thus, for example, in some cases, signal from particles bearing saturated binding of total Hb is detected, thereby providing a normalizing measure of the number of particles. The number of particles serves as an indirect normalizing measure of the amount of total hemoglobin bound at saturation because the average Hb binding to each particle is a known constant for a particular assay. Detection of the bound target A1c then provides a direct indicator of the fraction A1c by comparison with the number of particles present. The assay can be structured in a number of alternative ways, including as described below.

For reference, the amino acid sequence of hemoglobin beta chain (after post-translational removal of the N-terminal methionine) as referenced herein is:

```
                                          (SEQ ID NO. 1)
          10         20         30         40
     VHLTPEEKSA VTALWGKVNV DEVGGEALGR LLVVYPWTQR 50         60         70         80
     FFESFGDLST PDAVMGNPKV KAHGKKVLGA FSDGLAHLDN 90        100        110        120
     LKGTFATLSE LHCDKLHVDP ENFRLLGNVL VCVLAHHFGK 130        140        146
     EFTPPVQAAY QKVVAGVANA LAHKYH
```

Subsequences identified herein are with reference to the human hemoglobin beta chain sequence provided here as SEQ ID NO. 1.

A schematic example of a Hb A1c assay using TRF labeled beads is shown in FIG. 1. As illustrated, a TRF bead with attached anti-Hb antibodies is contacted with hemolyzed blood containing sufficient hemoglobin to saturate the binding sites on the bead. In blood samples, some of the bound hemoglobin will be A1c. Contacting the bound hemoglobin with anti-A1c-biotin results in formation of antibody-Hb-antibody sandwiches on the surface of the bead, with exposed biotin. As shown, the three beads from left to right have increasing percent A1c. The beads having A1c, and therefore having anti-A1c with exposed biotin, can then be immobilized for reading using, for example, a surface, such as a lateral flow strip surface, having a zone with immobilized streptavidin.

Figure 2:
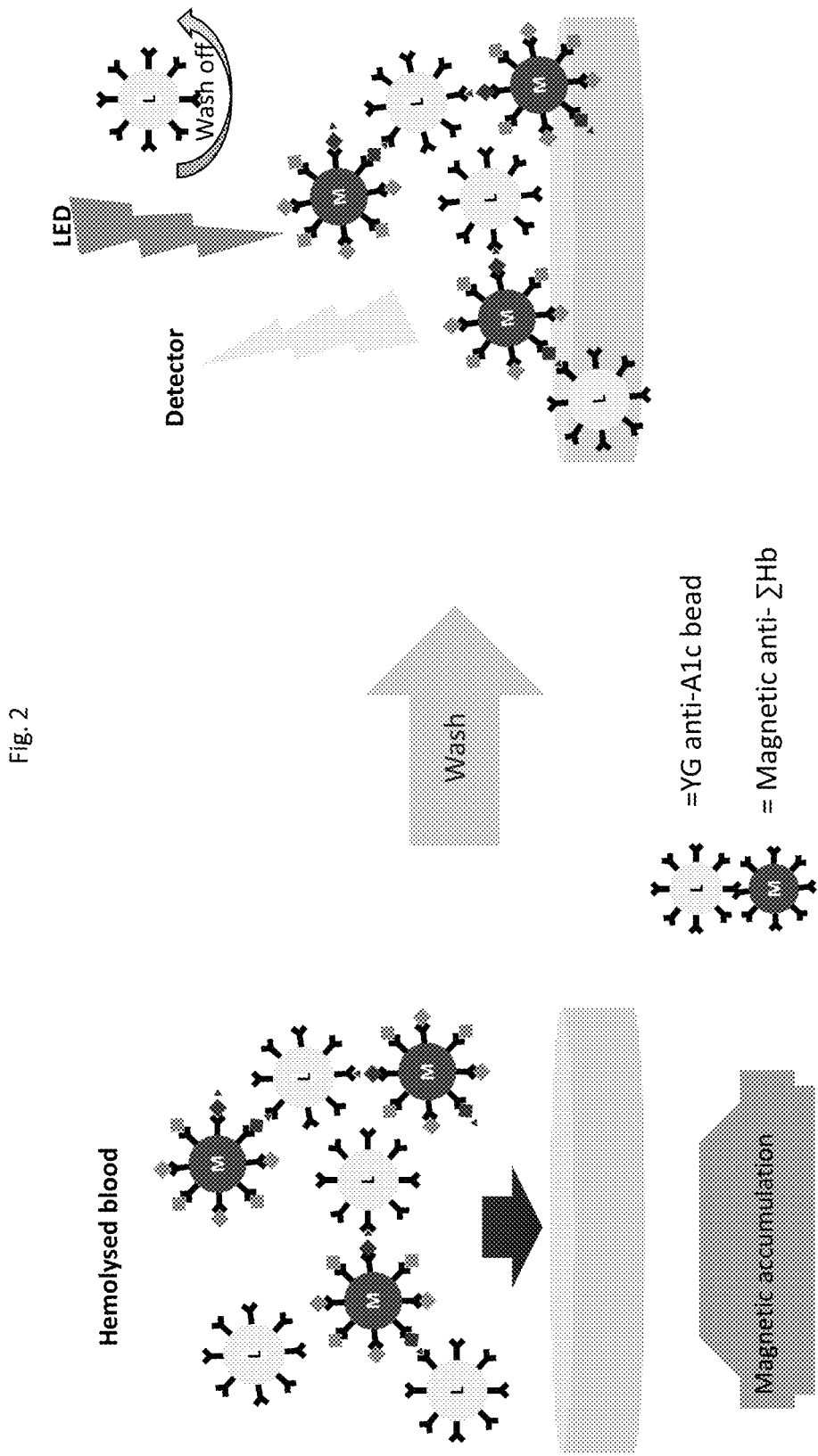
FIG. 2 schematically shows an A1c assay using saturation binding and magnetic immobilization of magnetic beads.

A similar Hb A1c assay is schematically illustrated in FIG. 2. In this assay, the anti-Hb beads are magnetic beads, and the label beads (which may be TRF beads) are anti-A1c beads. The anti-Hb magnetic beads are contacted with an excess of hemolyzed blood, resulting in saturation binding of Hb, including both HbA0 and HbA1 c. Contacting the anti-Hb beads with anti-A1c label beads results in formation of (Hb antibody)-A1 c-(A1c antibody) sandwich complexes containing both magnetic beads and label beads. The non-magnetic components (e.g., including unbound Hb and excess anti-A1c) can then be removed by immobilizing the magnetic beads with a magnetic field and washing away the non-magnetic sample components and reagents, and/or by moving the magnetic beads to a zone away from the non-magnetic components, e.g., using magnetic field(s). The signal from the A1c bound label beads can then be read as appropriate for the selected label type. When using advantageous anti-Hb which bind near the amino terminus of the Hb beta chain, the first wash is optional as described below.

In contrast to the present assays, an assay has been described in Maruo U.S. Pat. No. 5,593,480 which involves lysing red blood cells, pretreating the lysed blood with denaturing conditions to denature the hemoglobin, simultaneously adsorbing the denatured, hemolyzed blood, including Hb, on solid phase, e.g., particles, washing away the unbound hemoglobin, contacting the denatured blood with labeled anti-A1c antibody, and then washing away unbound labeled anti-A1c antibody. Detection of signal from the labeled Hb A1c antibody provides a measure of the fraction of Hb A1c in the sample. This method has limitations, including common non-specific binding of other blood components on the solid phase, which potentially interferes with Hb binding, the requirement for denaturing pre-treatment, and the need for multiple wash steps. The non-specific adsorption is not optimal because it reduces the possible load of detectible hemoglobin on each bead and adds potentially cross-reacting and otherwise interfering other non-specifically bound blood components on the beads. The need for the wash step after adsorbing the hemoglobin on the bead is undesirable because it results in loss of beads, commonly contributing to greater imprecision. The denaturing pre-treatment requires additional assay time and introduces a level of inconsistency in denaturation due to potential differences in blood samples. Advantageous embodiments of the present invention overcome those disadvantages.

B. Hemoglobin Assays

To develop a present assay based on labeled beads, e.g., TRF beads, an initial step can be to establish a dose response curve to identify the saturation plateau for the hemoglobin population. This can be accomplished by using uniform size beads, preferably labeled beads, which specifically bind total hemoglobin. The beads are preferably prepared such that the hemoglobin binding per bead is substantially constant, at least when averaged over multiple beads, e.g., at least 5, 10, 20, 50, or 100 beads. The labeled beads will, with small variation, produce the same signal level, so the total bead signal (verified to enhance precision) will be proportional to the number of beads added. The hemoglobin population is labeled, either pre-labeled or labeled after binding to the beads, e.g., using labeled second antibody. In this development step, unbound hemoglobin is removed, e.g., washed away or in the case of magnetic beads the beads can be moved to a detection zone, or solution containing the unbound hemoglobin not bound to magnetic bead can be displaced or washed away. Hemoglobin population signal is measured for increasing concentrations of hemoglobin population. Once saturation binding on the beads is achieved, the hemoglobin population signal per bead will plateau. The quantity of hemoglobin population per bead for use in the assay can then be adjusted, e.g., by adjusting one or more of sample dilution, sample volume, and bead number, such that binding saturation is achieved for the lowest hemoglobin population concentration to be encountered and stay constant throughout the hemoglobin concentration assay range.

For Hb, the concentration of Hb in different clinically relevant samples will be in the range of about 3 g/dl to about 30 g/dl. Thus, the indicated assay parameters can be adjusted so saturation binding is achieved for 3 g/dl samples. If desired, when carrying out the assays, a saturation binding control measurement may be performed by confirming the signal from hemoglobin population per bead matches the predetermined plateau level of the dose response curve. It is important to avoid hook effect or other non-linear binding interference which can occur when analyte concentration, i.e., hemoglobin concentration, is too high for the system.

For the assay, usually a known quantity of beads would be used, which would mean the population hemoglobin signal due to saturation binding would be known in advance from the saturation dose response curve. What remains is to measure the A1c subpopulation signal due to bound Hb A1c. This can be accomplished by using labeled specific binding molecule, e.g. an antibody or labeled boronate derivative, sufficiently specific for Hb A1c. The ratio of the signal due to A1c to the saturated hemoglobin population signal directly gives the ratio of A1c to total hemoglobin (with a constant proportionality factor). However, when the Hb is effectively normalized at saturation binding, the A1c ratio can be calculated as Ratio=(constant proportionality factor)×(signal A1c fraction)/(number of beads added). Alternatively the ratio of A1c to non-A1c can be readily calculated by subtracting the A1c fraction from the total Hb, and calculating the new ratio.

In some cases, the signal due to binding of A1c is measured by first separating bound hemoglobin from unbound hemoglobin, e.g., by immobilizing the bound hemoglobin (e.g., by immobilizing the beads which bear bound hemoglobin) and then measuring the signal from the bound A1c fraction of the bound hemoglobin. When using advantageous anti-Hb antibodies or other anti-Hb specific binding agent which also enhances exposure of the Hb A1c moieties, it is not necessary to wash away unbound Hb prior to contacting with anti-A1c. Instead, the unbound Hb and unbound anti-A1c can be washed away together in a single wash step. Alternatively, the signal due to bound A1c can be measured using a proximity signal, e.g., LOCI, FRET, TR-FRET, and the like. When carefully configured, such proximity signal assays can be carried out without needing to wash away either unbound hemoglobin or unbound anti-A1c prior to signal detection.

Several different variations of the present assay have been developed, and are described below.

1. Sample Treatment

For many samples, such as with blood samples, sample treatment is useful, e.g., including cell lysis. In most cases when determining fraction Hb A1c, a blood sample is used. The blood sample or resuspended cells are contacted under a red blood cell lysing condition. Such lysing agents, include, for example lysing detergents and/or lytic peptides. Often a red blood cell lysing agent or combination of agents is used, which often includes a suitable lysing detergent or detergent combination. Alternatively, or in combination with lysing agent(s), physical treatment may be used to lyse the red blood cells. Such physical treatments include but are not limited to freezing, electric shock, and sonication. The lysis releases the hemoglobin from the red blood cells. In many cases, the sample is contacted with the red blood cell lysing agent prior to being added to the assay device, e.g., as a sample pretreatment. However, the lysing agent may instead be included in an assay device. Numerous such red blood cell lysing agents are known and may be used. Suitable red blood cell lysing agents include, for example, Zwittergent, Triton X-100 and Igepal CA-630, lytic peptides such as melittin, and others are known to those of skill in the art and may be used.

In addition to lysis of cells, e.g., red blood cells, the sample treatment can include denaturing treatment (e.g., using chaotropic agents) to denature native hemoglobin (e.g., to dissociate the hemoglobin tetramer, and can further denature the beta chains).

However, in advantageous embodiments of Hb A1c detection, denaturation of the beta chains is not needed. Instead, exposure of the A1c binding epitope is enhanced by using a Hb binding agent, usually antibody, which binds near the beta chain terminal valine which is glycosylated in Hb A1c, generally binding within amino acids 3-30, more often within amino acids 7-25. Binding of the Hb antibody or other Hb binding agent causes the amino terminus to be exposed, making it available for efficient binding by anti-A1c antibody or other A1c binding agent. The antibody or other specific binding agent which binds in the indicated region near the beta chain amino terminus can thus be dual function. That is, the specific binding agent both binds the total hemoglobin to the solid phase, e.g., bead, and exposes the amino terminus, and also makes the A1c epitope available for more consistent and/or higher affinity binding with anti-A1c binding agent.

For Hb assays, the sample treatment may, in some cases, include dilution of the sample to provide appropriate reduced concentrations of Hb for detection, i.e., to bring the Hb concentration within the effective dynamic range of the assay. Thus, the dilution is selected to be compatible with the sensitivity and dynamic range of the assay to be used. For the present assays, this includes matching the dilution to the binding capacity of the beads to ensure saturation binding of analyte population without encountering hook effect or other non-linear binding effect of excessively high analyte concentrations. Commonly, dilutions of about 2×, 3×, 4×, or 5× are used.

2. Anti-Hb Antibody Binding Near Hb Beta Subunit Amino Terminus

As indicated above, in some highly advantageous embodiments anti-Hb antibody is used which binds near the Hb beta subunit amino terminus. Binding of selected antibodies allows isolation of antibodies which result in a conformational change which exposes the beta chain amino terminus, allowing efficient binding of anti-A1c antibody or other specific A1c binding agent. Thus, this approach does not require any general denaturing treatment, e.g., chaotrope treatment.

Such antibody can be isolated by immunizing with a peptide having a sequence corresponding to an amino acid sequence of the Hb beta subunit near the amino terminus. For example, such peptide may have sequence selected from within amino acids 3-30 inclusive or 7-25 inclusive. In most cases, the peptide used for immunization will be about 5-20, 5-15, 5-10, 5-9, 5-8, or any of integer lengths in the range from 5 to 20 amino acids in length (e.g., 5, 6, 7, 8, 9, 10, etc.). Examples of such peptides include or consist of amino acid residues 3-8, 7-11, 7-13, 9-13, 14-18, 19-23, 24-28, 3-12, 7-15, 7-16, 9-15, 9-18, 14-23, 19-28, 21-30, 3-16, 7-20, 9-22, 14-27, 17-30, 3-18, 7-22, 8-23, 9-24, 13-28, 3-20, 7-24, 8-25, 9-26, 13-30, 3-22, 7-25, 7-26, 9-28, 11-30, 3-27, 7-30, and 3-30. In many cases, the peptide will be attached to a linker, e.g., a PEG linker (for example, with about 5-20 subunits), and an adjuvant or carrier moiety, e.g., KLH, creating the immunogen.

Immunizing animals, such as mice, rats, or rabbits, with the immunogen results in development of a population of peptide-specific antibodies in the animal. Using conventional methods, antibodies, usually monoclonal antibodies, can be isolated which are specific for the peptide and bind an epitope which exposes the Hb amino terminus of Hb beta subunit to efficient binding with anti-A1c antibody or other A1c binding agent. Antibodies resulting from injections of immunogens which include peptides in the aa 3-30 and 7-25 range in mice have been shown to result in populations of antibodies which include antibodies which have the desired activity of exposing the beta subunit amino terminus allowing effective anti-A1c binding.

Antibodies which cause exposure of the amino terminus can be selected by testing co-binding of anti-A1c antibody. For example, binding of anti-A1c antibody in the presence of binding of the Hb-binding antibody can be compared to binding of the anti-A1c antibody to denatured Hb beta subunit. Similar levels of binding indicate the antibody is effective to expose the amino terminus for binding of anti-A1c.

It was discovered that Hb-binding antibodies which expose the A1c binding epitope can be selected which provide an additional beneficial effect. That is, for Hb bound to such anti-Hb antibody, binding of anti-A1c to HbA1c is sufficiently enhanced to allow binding of anti-A1c to Hb A1c bound to the anti-Hb, even in the presence of unbound A1c, which may even be a large excess of unbound A1c. The difference in binding affinity is sufficient that the concentration of anti-HbA1c can be adjusted to a level such that anti-HbA1c will bind to essentially all of the bound HbA1c (i.e., HbA1c already bound with anti-Hb), while binding of anti-HbA1c with unbound HbA1 c is minor. This means that detection of bound HbA1c can be performed even in the presence of some residual unbound HbA1 c, even a large excess of unbound HbA1c. For example, with anti-Hb attached to magnetic beads, and Hb (including some HbA1c), the anti-HbA1c will preferentially bind with the bound HbA1c over the unbound HbA1c. When there is not too great an excess of anti-HbA1c, essentially all HbA1c-anti-HbA1 c binding will be with bound HbA1c rather than free HbA1c. Thus, it is beneficial to select anti-A1c which does not significantly bind with free Hb A1c, so that the exposure of the Hb amino terminus upon binding of the Hb with the selected anti-Hb acts as an effective discriminator.

Without being limited to a particular mechanism, it is believed the anti-Hb antibodies which bind near the beta chain amino terminus cause a conformational change to the beta chain which causes the amino terminus to be exposed. For Hb A1c, the exposure of the beta chain amino terminus makes the A1c binding epitope more readily available for binding with anti-A1c antibodies or other anti-A1c binding agent than in the absence binding of the anti-Hb antibody near the beta chain amino terminus. The apparent conformational change exposing the anti-A1c binding epitope causes binding to A1c which is already bound with anti-hemoglobin to proceed faster than binding of anti-A1c to free Hb, and may also enhance binding affinity. In addition, when using a two-bead system, i.e., anti-Hb-bead with anti-A1c-label-bead, an additional mechanism can further stabilize and therefore favor the binding to complex. That is, both the anti-Hb beads and the anti-A1c beads will have multiple binding sites available. Therefore, the beads can form networks of multiple beads, thereby effectively locking beads in position and maintaining the (anti-Hb bead)-HbA1c-(anti-A1c-label bead) sandwich linkages. Such linkages are difficult to break up with free unbound A1c present in surrounding solution, thus allowing assays to be performed in high relative excess of free unbound A1c.

The indicated selections of anti-Hb and anti-A1c can beneficially provide at least 2, 5, 10, 20, 50, 100, 200, 500, or 1000-fold greater binding of the anti-A1c to bound Hb A1c as compared to unbound Hb A1c under assay conditions.

Preferably anti-Hb antibodies for use in the present assay are selected which have little or no binding with HbF. That is, anti-Hb antibodies are selected which preferentially bind Hb beta subunit rather than Hb gamma subunit. Thus, antibodies can also be counter-selected to have much lower, preferably substantially no, binding with HbF, i.e., with hemoglobin gamma subunit. Such antibodies which preferentially bind with beta subunit over gamma subunit can be selected from antibodies which bind within the amino terminal region indicated, e.g., within amino acids 3-30 or 7-25 inclusive, or with a subsequence thereof, such as within amino acids 3-8, 7-11, 7-12, 7-13, 8-12, 8-13, 9-13, 14-18, 19-23, 24-28, 3-12, 7-14, 7-15, 7-16, 7-18, 8-14, 8-15, 8-18, 9-15, 9-18, 14-23, 19-28, 21-30, 3-16, 7-20, 8-20, 9-22, 14-27, 17-30, 3-18, 7-22, 8-23, 9-24, 13-28, 3-20, 7-24, 8-25, 9-26, 13-30, 3-22, 7-25, 7-26, 8-27, 9-28, 11-30, 3-27, 7-30, or 3-30. It is also desirable for many implementations to have substantially equal binding (or at least consistently similar binding within a few-fold difference) with major hemoglobin isoforms, e.g., HbS, HbC, and HbE, as with HbA. Such substantially equal binding can be readily tested using conventional methods for anti-Hb antibodies to select particularly advantageous antibodies.

3. Assay Variations for Addition of Labeled Binding Member

One of the present assay variations involves the timing of addition of the labeled specific binding member binding to total hemoglobin.

In one variation, particles are contacted with the labeled specific binding member (e.g., antibody) for the target variant A1c before separating bound and unbound A1c population. That is, sufficient labeled binding member is added to bind with effectively all of the bound A1c from the sample solution. Then A1c (with bound labeled binding member) which is bound to the beads (or other solid phase surface) is separated from labeled binding member (some of which may be bound to A1c) which is not bound to the beads or other surface. The signal from only the labeled binding member bound A1c bound on the particles is then read.

In other variants, the labeled binding member is added after total hemoglobin is bound to the particles and optionally separated from total hemoglobin not bound to the particles. This variant is particularly applicable to use of antibodies as indicated above which bind hemoglobin and enhance binding of A1c with specific binding agent, e.g., anti-A1c antibody. With such antibodies, concentrations can be arranged so that it is not necessary to separate unbound A1c from A1c bound with anti-Hb as part of the total bound Hb before contacting with anti-A1c. It is likely the binding enhancement is due to enhanced exposure of the A1c binding epitope.

4. Assay Variation Using Initial Separation of Bound and Unbound A1c

A close variant of the preceding assay variation involves separating bound A1c from unbound A1c before contacting the bound A1c with labeled A1c-specific binding member, separating bound and unbound labeled specific binding members, and reading signal from the bound specific binding members.

5. Assay Variation Using Lateral Flow Configuration

The present assay can be performed using a lateral flow configuration by immobilizing particles on a membrane strip. This immobilization will therefore also immobilize the total hemoglobin bound to the particles. The particles may be immobilized either before or after contact with the sample containing the total hemoglobin. Binding of binding agent specific for A1c can be carried out substantially as described above and provides for detection of the bound A1c among the total bound Hb.

6. Assay Variation Using Proximity Label (e.g., FRET, TR-FRET, FP, LOCI, etc.)

It has been found the present assays can be carried out using proximity labels, such as, FRET, TR-FRET, EMIT, Luminescent Oxygen Channeling Assay (LOCI), and multiple component enzyme label systems such as CEDIA (see, e.g., Henderson et al, CEDIA, a new homogeneous immunoassay system, *Clin Chem*, 1986, 32(9):1637-41). These proximity label configurations allow the assays to be carried out in a homogenous manner.

The proximity label approach can be described using a LOCI implementation. In such case, acceptor bead with bound anti-hemoglobin is incubated with hemolyzed blood (which may be diluted) and anti-A1c antibody with attached biotin moiety. The hemoglobin (including Hb A1c binds to the acceptor bead, and anti-A1c binds to the A1c subpopulation of the bound hemoglobin. Addition of donor bead with attached streptavidin links acceptor bead and donor bead in close proximity. Upon illumination with light of an appropriate excitation wavelength (680 nm laser in this case), the donor bead emits singlet oxygen, which diffuses to and reacts with linked donor bead and causes the emission of detectable light (luminescence) from the acceptor bead.

More generally, when the LOCI donor label is contacted with light of a wavelength appropriate for that label, the donor label generates singlet oxygen. Because singlet oxygen has a very short lifetime in aqueous medium, it will only elicit light emission from the acceptor label if the distance between donor and acceptor labels is short, i.e., if donor label is linked with acceptor label in close proximity through analyte, so that the singlet oxygen can react with the acceptor before quenching. For antibody-acceptor label conjugate which is bound only with analyte from the sample, no light emission will occur because there is not closely linked LOCI donor label (i.e., singlet oxygen generator).

As a result, when the completed binding mixture is illuminated with light of a wavelength suitable for generating singlet oxygen from the LOCI donor label, the intensity of the emitted light signal will be directly related to the concentration of the analyte in the binding reaction mixture. This type of donor and acceptor label set can be used in the present A1c assays. For example, the signal corresponding to the A1c subpopulation directly correlates with the A1c subpopulation fraction.

In some cases, the assay using LOCI provides high precision, giving results for the calculated HbA1 c percentage with a CV of less than 3.0, 2.7, 2.5, 2.3, 2.1, 2.0, 1.9, 1.8, 1.7, 1.6, or 1.5%, based on a minimum of 20 replicates.

The following descriptions are provided to increase the understanding of a number of different proximity label systems.

a. Enzyme Multiplied Immunoassay EMIT

The EMIT assay is a homogeneous enzyme immunoassay (EIA). Typically the assay uses an excess of specific antibodies that bind with the analyte being measured, which are added to a liquid sample. If the target analyte is present, the analyte molecules bind to the antibody sites. Enzyme labeled analyte construct is added, where the binding of this construct to the antibody inhibits enzyme activity. The extent of binding of the construct to the antibody molecules will be inversely proportional to the concentration of analyte in the sample, and therefore will also be inversely proportion to the signal resulting from the activity of the free enzyme labeled analyte construct. That is, binding of the enzyme labeled analyte construct to the antibody binding sites not previously filled be sample analyte reduces the total signal from the enzyme. In most cases, the system produces a colorimetric signal.

b. Fluroescence Resonance Energy Transfer (FRET)

While Fluorescence Resonance Energy Transfer (FRET) may be used for generating the proximity signal, Time Resolved-Fluorescence Resonance Energy Transfer (TR-FRET) is said to be emerging as one of the preferred assay formats in drug discovery laboratories. An example of such an assay is the LanthaScreen™ from Invitrogen.

The LanthaScreen™ format is based on the use of a long-lifetime terbium chelate as the donor species and fluorescein as the acceptor species. When terbium and fluorescein labeled molecules are brought into proximity, energy transfer takes place causing an increase in acceptor fluorescence and a decrease in donor fluorescence. These fluorescent signals can be read can be read in a time-resolved manner to reduce assay interference and increase data quality. The TR-FRET value is determined as a ratio of the FRET-specific signal measured with a 520 nm filter to that of the signal measured with a 495 nm filter, which is specific to terbium.

Other TR-FRET assays have used europium as the 'long lifetime label' and allophycocyanin (APC) as the donor species. Due to the large molecular mass of APC (>100 KD) it has typically been used as a streptavidin conjugate, to indirectly couple to the biotinylated substrate in a trimolecular FRET complex.

c. Fluorescence Polarization (FP)

Fluorescence polarization assays are based on the different polarization of the fluorescent output of bound versus unbound fluorescent species.

Fluorescence polarization (FP) is based on the observation that when a fluorescent molecule is excited by plane-polarized light, it emits polarized fluorescent light into a fixed plane if the molecules remain stationary between excitation and emission. Because the molecule rotates and tumbles in space, however, FP is not observed fully by an external detector. Light is differentially absorbed by molecules as a function of their orientation relative to the direction and polarization of the exciting light. The light subsequently emitted as fluorescence by each of the resulting electronically excited molecules will usually be polarized. Rotation during the lifetime of the excited states randomizes the orientation of the excited molecules leading to a net reduction in fluorescence polarization. The more rapid the tumbling the less polarization is observed. Fluorescence polarization immunoassay (FPIA), has been applied in the detection of analyte in a homogeneous assay format.

The FP of a molecule is proportional to the molecule's rotational relaxation time (the time it takes to rotate through an angle of 68.5°), which is related to the viscosity of the solvent, absolute temperature, molecular volume, and the gas constant. Therefore, if the viscosity and temperature are held constant, FP is directly proportional to the molecular volume, which is directly proportional to the molecular weight. FP of a large molecule is (with high molecular weight) is preserved because the molecule rotates and tumbles more slowly in space, while FP is largely lost (depolarized) for a small molecule (with low molecular weight), because small molecules rotates and tumbles faster. The FP phenomenon has been used to study protein-DNA and protein-protein interactions, DNA detection by strand displacement amplification, and in genotyping by hybridization.

This phenomenon was first applied in a homogeneous immunoassay by Dandliker (Dandliker, et al, 1961, 1973) but the method was initially little more than a laboratory curiosity because of the primitive state of development of commercial spectrofluorometers and the requirement for two separate measurements differing by a 90° rotation of a polarizing lens. Currently, over fifty fluorescence polarization immunoassays (FPIA) are commercially available, many of which are routinely used in clinical laboratories for the measurement of therapeutics, metabolites, and drugs of abuse in biological fluids.

Fluorescence polarization immunoassay (FPIA), has been applied almost exclusively to small molecule analytes. The sample and antibody are combined and the antigen in the sample competes with fluorescer-labeled antigen for binding to the antibody. Increasing concentrations of the antigen produce decreased polarization. Abbott Laboratories uses FPIA primarily for therapeutic drug monitoring and drug abuse testing on their TDx immunochemistry system. The success of the method after years of disuse stemmed in larger measure from the development of improved solid state methods for analyzing polarized light.

Interference from adventitious fluorophores and non-specific binding of the label to proteins as well as shielding the fluorescence signal by materials in biological samples has restricted the detection limit of FPIA to concentrations of above 100 pM. By using a highly hydrophilic long wavelength dye and time delayed measurements that permit discrimination between the emission from the background and the label, detection of concentrations down to 1 fM have been claimed (Devlin et al 1993). Exchanging the detection solution to maximize the efficiency of the signal would provide extremely advantageous environment to detect the unknown analyte at extremely low concentrations.

FP is expressed as the ratio of fluorescence detected in the vertical and horizontal axes and, therefore, is independent of the fluorescence intensity. This is a clear advantage over other fluorescence detection methods in that as long as the fluorescence is above detection limits of the instrument used, FP is a reliable measure.

Dandliker, W. B. & Feigen, G. Quantification of the antigen-antibody reaction by the polarization of fluorescence. *Biochem. Biophys. Res. Commun.* 5, 299 (1961).

Dandliker, W. B., Kelly, R. J., Dandliker, J., Farquhar, J. & Levin, J. Fluorescence polarization immunoassay. Theory and experimental method. *J. Immunochemistry* 10, 219-227 (1973).

Devlin, R., Studholme, R. M., Dandliker, W. B., Fahy, E., Blumeyer, K. & Ghosh, S. S. Homogeneous detection of nucleic acids by transient-state polarized fluorescence. *Clinical Chemistry* 39, 1939-1943 (erratum 2343), (1993).

Guo, X-Q., Castellano, F. N., Li, L., Lakowicz, J. R. Use of a long-lifetime Re(I) complex in fluorescence polarization immunoassays of high molecular weight analytes. *Anal. Chem.* 70, 632-637 (1998).

d. Luminescent Oxygen Channeling Assay (LOCI)

The present invention can advantageously be applied to a homogeneous assay method referred to as Luminescent Oxygen Channeling Assay (LOCI™ (Behring Diagnostics)), which is based on chemiluminescence. Generally, the assay generates a signal resulting from close approach of a photosensitizer moiety and a chemiluminescer. (See, e.g., Ullman, 1994, Proc Natl Acad Sci, USA 91:5426-30; Ullman et al., 1996, Clin Chem 42(9):1518-26; Ullman et al., U.S. Pat. No. 6,406,913, all of which are incorporated herein by reference in their entireties.) Upon irradiation with light, the photosensitizer produces singlet oxygen, which initiates luminescence from the chemiluminescer. Due to the dilution effect as the single oxygen diffuses away from the sensitizer and the short lifetime of the singlet oxygen, the effect is strongly dependent on the distance between the sensitizer and the chemiluminescer. Therefore, substantially all of the observed luminescence will be due to sensitizer/chemiluminescer pairs that are co-bound with an analyte.

e. Enzyme Channeling

An assay format conceptually similar to LOCI is enzyme channeling. Enzyme channeling provides a method of detecting the proximity of two enzymes in an immune complex. The first enzyme catalyzes the formation of a substrate that is converted by the second enzyme into a detectable product. When both enzymes are independently dispersed in the same solution the rate of product formation is slow at first but accelerates as the concentration of the intermediate substrate builds up. This kinetic behavior changes when both enzymes are closely associated at a surface (Mosbach and Mattiasson, 1970). The local concentration of the intermediate in the vicinity of molecules of the first enzyme is determined by the rate of formation of the intermediate and its rate of diffusion away from the enzyme. A local steady state concentration is rapidly reached that is higher than the concentration in the bulk solution. Localization of several molecules of the first enzyme at a surface increases the rate of product formation and reduces the rate of product diffusion and thus increases its local concentration. When the second enzyme becomes bound to this surface it experiences a relatively constant elevated concentration of its substrate leading to a rapid linear rate of formation of the final product.

Homogeneous enzyme channeling immunoassays take advantage of this phenomenon (Litman, et al., 1980). Various surfaces have been employed including agarose particles, latex beads, and the polystyrene surface of a microtiter well. One enzyme serves to label an antibody or antigen and an excess of the other enzyme is bound to the surface. Usually the first enzyme is attached to the surface because more linear kinetics are obtained although channeling also occurs when the roles of the enzymes are reversed. A variety of enzyme pairs have been used including alkaline phosphatase/β-galactosidase, hexokinase/G6PDH, and glucose oxidase/HRP. When a natural substrate is not available as in the case of alkaline phosphatase/□-galactosidase synthetic constructs can be prepared that permit the sequential reaction to occur.

A competitive assay for HIgG can be carried out with agarose particles labeled with HIgG and glucose oxidase (GO). Upon reaction with glucose these particles become surrounded by a halo of hydrogen peroxide. As the peroxide diffuses into the bulk solution it is diluted and the concentration is further reduced by catalase that is present in the reaction mixture. When HRP-labeled anti-HIgG antibodies bind to the particles in the presence of ABTS, an HRP substrate, there is a nearly constant rate of color formation that depends inversely on the concentration of the HIgG.

The most sensitive applications of enzyme channeling avoid the use of a pre-formed surface in favor of in situ formation of a colloidal precipitate. An assay for polyribose phosphate (PRP), a component of the cell wall of *Haemophilis influenzae*, was demonstrated using a reagent containing anti-PRP antibody labeled with GO (AB-GO), anti-PRP antibody labeled with HRP (Ab-HRP), and free GO (Ullman, et al, 1984). Combination of this reagent with a clinical sample to which anti-GO antibody had been added produced an Ab-GO:PRP:Ab-HRP sandwich complex that was incorporated into a colloidal GO:anti-GO immune complex (precipitin). Addition of glucose, ABTS, and catalase initiated the enzyme channeling reaction. The assay response was nearly linear with a detection limit of about 10 fM PRP in the assay mixture, sufficient for a cerebral spinal fluid assay for bacterial meningitis. Unfortunately there has been little study to determine if similarly sensitive homogeneous enzyme channeling immunoassays can be carried out using serum samples.

Litman, D. J., Hanlon, T. M. & Ullman, E. F. Enzyme channeling immunoassay: a new homogeneous enzyme immunoassay technique. *Anal. Biochem.* 106, 223-229 (1980).

Ullman, E. F., Gibbons, I., Weng, L., DiNello, R., Stiso, S. N. & Litman, D. Homogeneous immunoassays and immunometric assays. In *Diagnostic Immunology: Technology Assessment and Quality Assurance*. Eds. Rippey, J. H. & Nakamura, R. M., 31-46 (College of American Pathologists, Skokie, Ill., 1984).

f. Two-Component Enzymatic Label (CEDIA)

CEDIA (Cloned Enzyme Donor Immunoassay) assays utilize two genetically engineered, enzymatically inactive fragments of beta-galactosidase as the basis for a homogeneous enzyme immunoassay. The smaller, amino-terminal polypeptide, designated the enzyme donor (ED), can recombine spontaneously with the large residual fragment, called the enzyme acceptor (EA), to form active beta-galactosidase, in a process called complementation. ED have been designed in such a way that a ligand, such as a hormone or drug, can be chemically attached to a specific amino acid residue without affecting the enzyme complementation. However, the binding of a ligand-specific antibody to the ED-ligand conjugate will inhibit complementation. If a sample containing ligand is added to the reaction mixture, the ligand will compete with the ED-ligand conjugate for the limited number of antibody binding sites. Thus, the ligand concentration in the sample will modulate enzymatic activity by influencing the amount of free ED-ligand conjugate available for complementation. The basic technology of CEDIA assays has a number of inherent characteristics, the most important of these being a linear calibration curve with high precision over the whole assay range, lack of endogenous enzyme activity and minimal serum interference, chemically defined conjugates and flexibility in assay design. These provide significant benefits in comparison to some of the other homogeneous immunoassay techniques.

Henderson et al, CEDIA, a new homogeneous immunoassay system, *Clin Chem,* 1986, 32(9):1637-41.

Engel & Khanna, CEDIA in In vitro diagnostics with a novel homogeneous assay technique. Current Status and future prospects, *J Immunol Methods,* 1992, 150(1-2):99-102.

7. Magnetic Bead Separation Saturation Assay.

Another variation of the present assays using magnetic beads and magnetic fields to separate labeled magnetic beads saturated with bound total hemoglobin, some of which may be the A1c sub-population(s) of interest, from interfering signals. The total hemoglobin can be attached to the beads in various ways, e.g., with specific binding agent or electrostatically. For electrostatic binding, the beads and the hemoglobin will have opposite net charge, thereby causing an attractive interaction, which can be varied by varying the solution pH. In many implementations, however, the hemoglobin is attached using anti-total hemoglobin, advantageously an anti-total hemoglobin binding agent (most often antibody) which binds in the beta chain amino terminal region as described herein.

Labeled first specific binding agent binds to the hemoglobin, including the Hb A1c sub-population(s) of interest, both hemoglobin bound to beads (including the A1c fraction of the total analyte) as well as that not bound to beads. When using anti-Hb antibody as described which binds near the amino terminus, binding of the anti-A1c second specific binding agent to Hb A1c is strongly in favor of binding to hemoglobin A1c which is bound with anti-total hemoglobin over binding with A1c which is free. In most cases, the labeled second specific binding agent (anti-A1c) is provided in excess to ensure substantially all of the A1c subpopulation bound on the beads is bound with anti-A1c. The labeled second specific binding agent is labeled directly (e.g., with a dye) or indirectly (e.g., with biotin which will bind with streptavidin linked with a dye). If the magnetic beads are labeled, the label signal from the labeled second specific binding agent should be distinguishable from the signal from the labeled magnetic beads.

Individuals familiar with assay labels will readily recognize various options for suitable distinguishable label combinations. As non-limiting examples, the label on and/or in the labeled magnetic beads may be fluorescent dye or combination of dyes or an absorbance dye or quantum dot label or TRF label. The label or labels directly or indirectly attached to the labeled second specific binding agent produces a signal, distinguishable from the signal from the labeled magnetic beads. For example, labels may be distinguishable based on different emission wavelengths and/or different timing of light emission (e.g., fluorescent versus phosphorescence (TRF) and/or on light emission versus light absorption.

The timing of the respective binding events can be arranged in different ways as desired for a particular assay. For example, total hemoglobin may be bound to the labeled beads first, e.g., using first specific binding agent, followed by binding of the labeled second specific binding agent to bound A1c subpopulation. Alternatively, labeled second specific binding agent may be bound with A1c subpopulation, and then total hemoglobin is bound to the labeled complexes. In another alternative, sample containing total hemoglobin, labeled beads which bind with hemoglobin such as using first specific binding agent, and labeled second specific binding agent are combined substantially simultaneously, and binding of hemoglogin and binding of anti-A1c to Hb A1c occurs in the same solution.

Generally, the present assay methods using magnetic or charged particles such as beads involve saturated binding of total hemoglobin to beads which can be moved and/or held in a controlled fashion, e.g., magnetic bead which can be moved or held using magnetic fields) or charged beads which can be moved or held using electric fields. While the discussion herein emphasizes use of magnetic beads, it should be understood the assay configurations described also apply to embodiments in which charged beads and electric fields are used instead.

In addition to creating sandwich complexes which include labeled bead (e.g., labeled magnetic bead), bound total hemoglobin, and bound labeled second specific binding agent, for most types of labels it is necessary to separate labeled second specific binding agent which is not linked to beads (e.g., magnetic beads) and is therefore not part of the sandwich complexes, from labeled second specific binding agent which is part of the sandwich complexes. Such separation substantially eliminates the confounding signal from unbound labeled second specific binding agent and labeled second specific binding agent which is free or is bound to A1c subpopulation but not bound in sandwich complexes.

The separation can, for example, be carried out by using a magnetic field to move the magnetic beads (or electric field to move the charged beads), or the beads can be held in place and the solution containing labeled second specific binding agent not linked to magnetic (or charged) bead exchanged with medium not containing such uncomplexed labeled second specific binding agent.

In cases in which the beads are moved, the beads can be moved into new medium, e.g., in a reading zone. In this way, the signal read from labeled second specific binding agent will only be due to labeled second specific binding agent which is in sandwich complexes and therefore corresponds to the proportionately bound A1c subpopulation.

8. Two-Bead Linear Response Using Magnetic Bead Binding Hemoglobin and TRF Beads Binding Hb A1c.

Demonstration tests have been performed using two-bead sandwich binding as illustrated in FIG. 2, with magnetic beads binding Hb, and TRF beads binding Hb A1c. In one test, solutions with three different concentrations of Hb A1c were tested and test spots were imaged and scanned. The respective spots qualitatively showed brightness corresponding to the respective A1c concentrations, and the qualitative results were confirmed with a scanner able to detect the signal from the label. Similarly, a test was performed using multiple solutions covering a clinically relevant range of A1c concentrations. This demonstration test showed an essentially linear relationship for label signal to A1c concentration with saturated binding of Hb. These tests demonstrate that for antibodies selected to have separated binding sites, the presence of saturated binding of Hb to Hb antibody does not interfere with the proportional binding of anti-A1c antibody to Hb A1c present as a subpopulation in the total Hb population.

9. Examples

Hb A1c assays implementing the present invention have been performed using TRF label in lateral flow format, using magnetic beads, and using LOCI. Examples of assays with results are described below.

Example 1: Assay with Magnetic Anti-Hemoglobin Particles

Assays were carried out using magnetic beads bearing surface anti-total hemoglobin antibodies as schematically shown in FIG. 2. The antibodies were obtained from mice using an immunogen containing hemoglobin beta chain amino terminal peptide and selected as described above, such that the antibodies bind with an epitope within amino acids 7-25 of the hemoglobin beta chain and cause exposure of the beta chain amino terminus. The magnetic beads used were 200 nm. The assays were carried out as dry A1c assays, meaning reagents were provided in dry form (as fast reconstituting reagent pellets) and were reconstituted in the assay device during the performance of the assay. To carry out the assays, sample was introduced into a first assay device chamber, thereby reconstituting dry anti-Hb magnetic beads within the chamber, and incubated for 60 s, followed by mixing in the same chamber for 90 s. The magnetic beads were then moved to a second chamber containing dry labeled anti-A1c, thereby reconstituting the anti-A1c reagent. The anti-A1c reagent was made of dyed polystyrene particles 1 micron in diameter, coated with anti-A1c antibody raised against glycated N-terminus comprised of two amino acids. The resulting solution was incubated for 60 s, followed by mixing for 90 s. The magnetic beads were immobilized with a magnetic field for 120 s, followed by a 3 min wash. The resulting A1c label signal from the immobilized beads was read.

Figure 3:
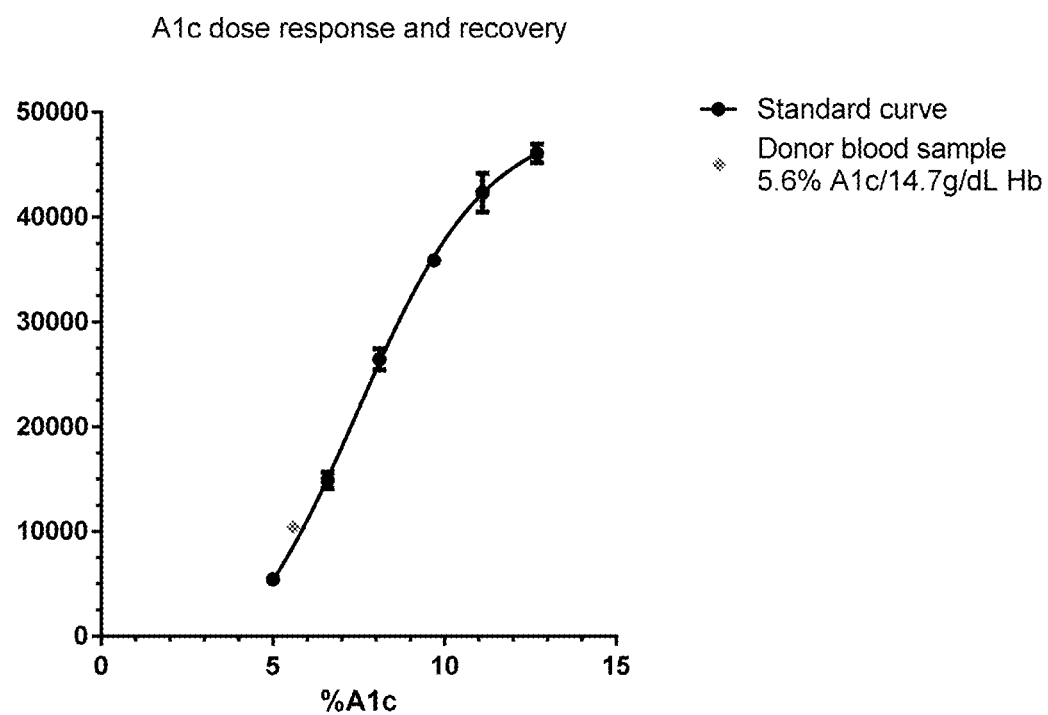
FIG. 3 is a graph showing donor blood sample A1c results determined using a magnetic bead saturation A1c assay matched to a dose response standard curve.

From the results, a curve was created using a set of in house made frozen blood A1c calibrators which had an A1c range from 3.9 to 12.7%. Demonstration assay was performed with donor control sample. The signal obtained from the control clinical sample showed appropriate recovery against the dose response curve. Results are shown in FIG. 3.

Similarly, assay was run with A1c calibrators derived from commercial sources. FIG. 4 shows dose response to lyophilized blood calibrators (Biorad Lyphocheck) and intact red blood cell A1c calibrators (Strek Cellular).

Figure 5:
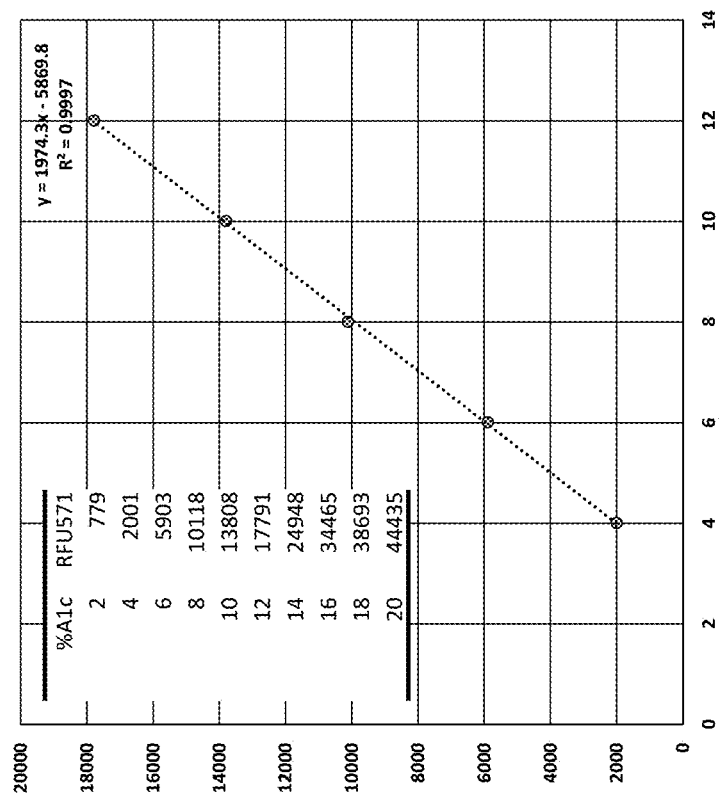
FIG. 5 shows graphed assay results with synthetic A1c calibrators in a magnetic bead saturation A1c assay.

The assay was also successfully performed with synthetic A1c calibrators comprised of linked A1c and HbA0 epitopes. FIG. 5 shows linear dose response to such calibrators blended with non-glycated variant to artificially create different A1c ratios.

Figure 6:
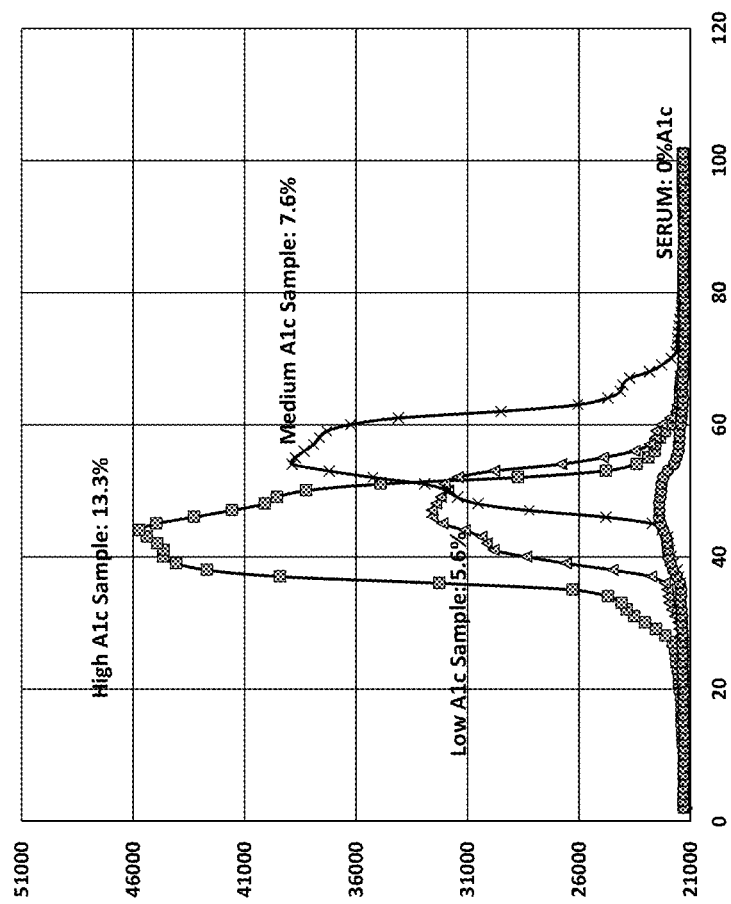
FIG. 6 shows scan results with fresh lysed blood in a magnetic bead saturation A1c assay.

Finally, the assay was run with lysed freshly drawn blood. The lysis was performed with 0.5% Zwittergent or Deoxycholate solutions. FIG. 6 demonstrates progressive increase in signal from three samples at low, medium and high A1c levels.

These assay examples illustrate that the present A1c assays can be effectively performed as dry assays on three different types of A1c standard samples, as well as on freshly drawn lysed blood.

Figure 7:
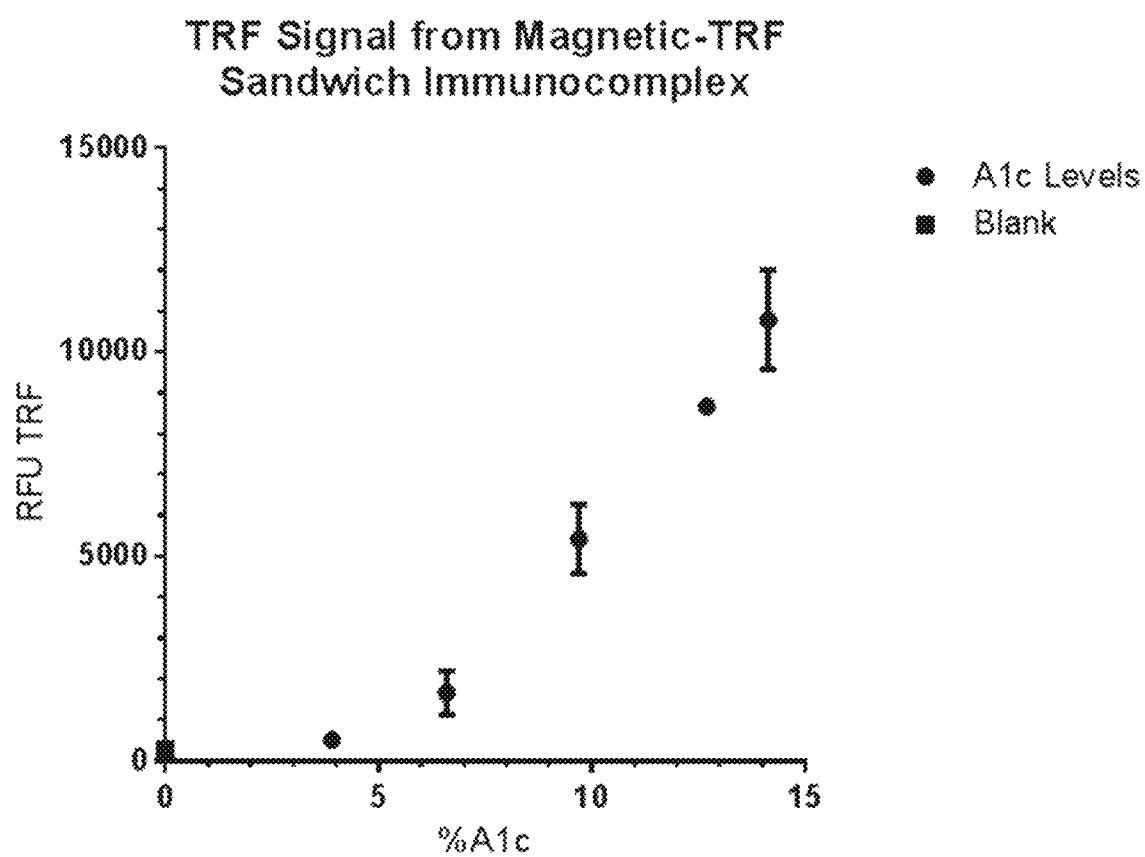
FIG. 7 is a graph showing results of a magnetic bead saturation A1c assay using undiluted blood samples.

Example 2: Assay with Magnetic Anti-Hemoglobin Particles and Undiluted Blood Sample A magnetic bead assay has been carried out using undiluted blood. For these assays, we used six different undiluted frozen blood samples, which contained 0, 3.9, 6.6, 9.7, 12.7, and 14.4% A1c respectively. The assays were carried out per FIG. 2, wherein magnetic beads modified with anti-total hemoglobin antibody were mixed with hemolyzed whole blood at 14 g/dL hemoglobin. After 5 min incubation, the excess blood was removed from magnetic beads by magnetic separation and the beads were washed 2 more times with a buffer. Time resolved fluorescent (TRF) beads modified with anti-A1c antibody were added to the washed magnetic beads. After 5 min incubation the unbound TRF beads were washed thrice with buffer with an aid of a magnet. The TRF signal from magnetic-TRF sandwich immunocomplexes was recorded in a TRF reader. The results shown in FIG. 7 demonstrate that the present assays can be effectively carried out using undiluted blood in magnetic-TRF sandwich immunoassay.

Example 3: Lateral Flow Hb A1c Assay

Another illustrative assay has been carried out using TRF label in lateral flow configuration.

Figure 8:
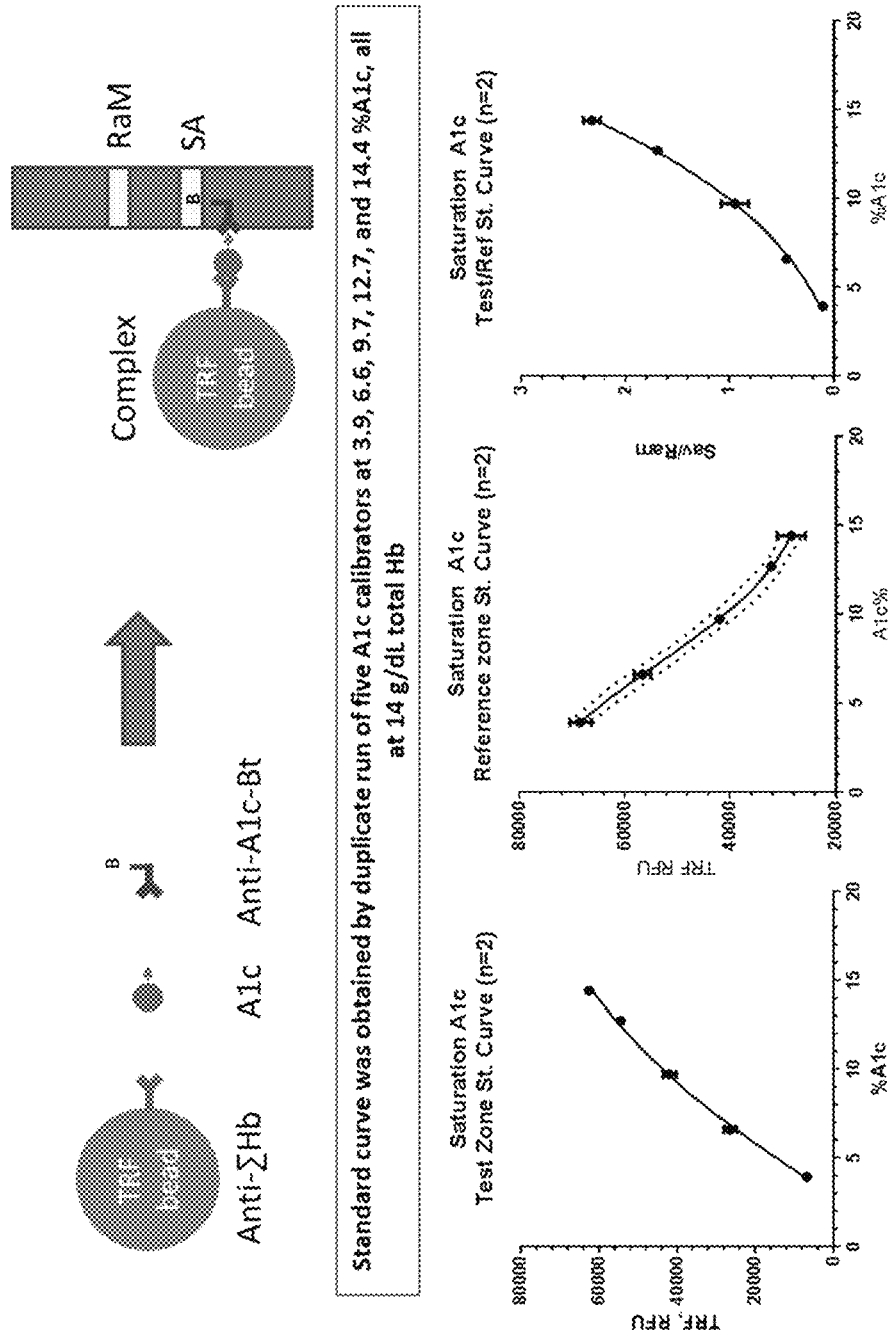
FIG. 8 shows a schematic illustrating the present assay in lateral flow configuration, with graphs showing assay results.

In lateral flow assay format, 5 uL of hemolyzed A1c calibrators were mixed with 3 uL of 100 ug/mL time resolved fluorescent (TRF) beads modified with anti-total hemoglobin antibody. After 5 min incubation at room temperature (rt), 2 uL of 35 ug/mL biotinylated A1c antibody was added followed by additional 5 min incubation at room temperature (rt). The reaction mixture was then allowed to run by capillary forces up a nitrocellulose membrane strip containing test streptavidin zone and a reference anti-mouse antibody striped zone. The reference zone is designed to capture any excess of unbound beads modified with mouse anti-total hemoglobin antibody. The reaction mixture was finally chased with an elution buffer to clear unbound particles. The finished and dried strips were read in a TRF reader to provide results shown in FIG. 8. Dose responses from both test and control zone were recorded and found to correlate with % A1c in each sample.

Example 4: Energy Transfer Hb A1c Assay

Yet another illustrative assay has been shown using, energy transfer label, in this case, LOCI. Anti-total hemoglobin antibody was conjugated to the surface of LOCI acceptor particles. The reactions were conducted in the wells of low volume white 384-well Proxi plate. Two microliters of anti-Hb acceptor particles diluted to 10 ug/mL was added to 16 uL of A1c samples having variable % A1 c from 3.9% to 14.4% and diluted at least 500× from whole blood. After 1.5 hrs incubation at 37 C, 2 uL of biotinylated anti-A1c antibody was added to the above reaction mixture. After 30 min incubation at 37 C, 2 uL of LOCI donor particle modified with streptavidin (10 ug/mL) was added to the reaction mixture. After 20 mi incubation at 37 C, the luminescent signal was recorded in Perkin-Elmer Alpha Fusion spectrophotometer. LOCI assay is a proximity assay whereby the signal is generated only when LOCI acceptor and donor particles are positioned in close proximity to each other which is achieved via immunoassay sandwich formation.

Figure 9:
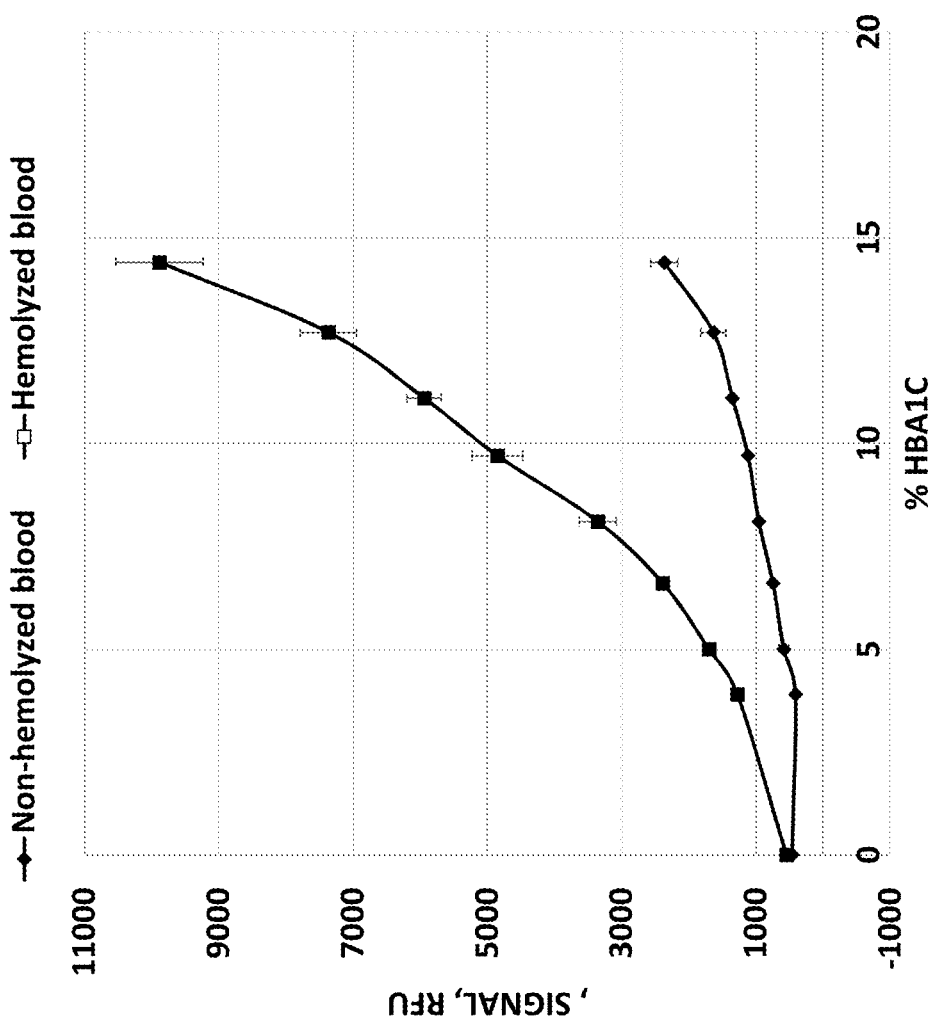
FIG. 9 is a graph showing assay results using an energy transfer label, with both hemolyzed and non-hemolyzed blood samples.

The results in FIG. 9 show corresponding responses in hemolyzed vs. non-hemolyzed blood samples. In case of hemolyzed samples, whole blood was hemolyzed with 1% zwitterionic detergent and then diluted to desirable concentration. Non-hemolyzed blood was diluted to same concentration as is. It is clear from FIG. 9 that the assay response was much more significant in hemolyzed blood.

Example 5: Magnetic Bead Test of Assay Anti-A1c Levels

Tests were performed to determine suitable levels of anti-A1c needed to bind with the A1c fraction of hemoglobin immobilized on magnetic beads. The hemoglobin was immobilized with antibodies which bind within the aa 7-25 region of the Hb beta chain amino end. The tests used 200 nm latex magnetic beads, and 1 μm latex label beads. One such test with calculations and results is shown below.

The very surprising and highly useful result showed that the assay worked properly even when there was a 1600× excess of free over magnetic bead-bound A1c, and a 250× excess of total A1c over anti-A1c antibody. That is, even in the presence of a large excess of free A1c, under the assay conditions and timing, anti-A1c binding to the immobilized A1c was sufficient for the assay. The conclusion is that anti-A1c binding to A1c using amino terminus anti-hemoglobin antibodies is highly preferred over binding to free A1c.

The test assays were carried out generally as described in Example 2, except there was no wash step performed to wash away unbound Hb prior to contacting the Hb bound to anti-Hb magnetic beads with anti-A1c TRF beads. The samples used for the test contained 14 g/dL Hb, 5.5% A1c. To perform the test, 250 nL of sample was mixed with 250 nL of 0.2% magnetic beads (200 nm beads) bearing anti-total hemoglobin and incubated to allow maximal binding of hemoglobin. The magnetic beads with bound hemoglobin were then contacted with 300 nL of 0.3% 1 um TRF-labeled latex beads bearing anti-A1c, still in the presence of unbound hemoglobin (which includes 5.5% A1c). After incubation to allow binding of anti-A1c to A1c, unbound anti-A1c beads were washed away, magnetic bead complexes were immobilized by applied magnetic field, and the signal from the bound anti-A1c latex beads was read. The results were consistent with results found for assays conducted in which unbound Hb (including unbound Hb A1c) was washed away prior to contacting the magnetic beads with anti-A1c label.

Preliminary calculations for the number of Hb molecules showed:
  1 uL sample=6.5E13 A1c molecules
  250 nL sample=1.6E13 A1c molecules
  250 nL of 0.2% Mag=0.5 ug of 200 nm magnetic beads.
  0.5 ug of 200 nm mags=1.1E8 beads.
  Max Ab capacity=1.6E3 Abs/bead.
  0.5 ug mags=max 1.8E11 antibodies per 3.3E14 Hb molecules; i.e. 1,800× excess of Hb over anti-Hb Ab.
  300 nL of 0.3% 1 um latex=0.9 ug of 1 um latex beads.
  0.9 ug 1 um latex=1.6E6 beads.
  Max Ab capacity=3.9E4 per bead.
  0.9 ug latex=max 6.4E10 Abs per 1.6E13 A1c molecules.=>250× excess total A1c over anti-A1c Ab.
  1,600× ratio of free over mag-bound A1c Since the assay works, and gives appropriate A1c percent with a large excess of free A1c over anti-A1c, we infer that conformational change is responsible for increased activity of bound A1c. We further conclude A1c assays can be carried out effectively with an excess of free A1c over anti-A1c, even without washing away the excess free A1c prior to contacting bound Hb with anti-A1c. This advantageous characteristic allows assay kits, e.g., assary cartridge, to be configured with much lower quantify of anti-A1c reagent. This is particularly beneficial for incorporating dry anti-A1c reagent (e.g., as dry pellets) within the assay cartridges.

Definitions

The term "label" is used in a manner common for biological or biochemical in vitro assays, and refers to a moiety of a molecule or complex that is directly or indirectly detectable in a manner providing detection of the presence or amount of the label present. Examples include fluorophores, chemiluminescent moieties, light absorbing moieties, resonance light scattering particles, enzymes, and the like, as well as specific binding moieties such as biotin, HA-tag (human influenza virus hemagglutinin), His-tag, Myc-tag, FLAG-tag, or other tag which can be used to link another moiety for detection. As used herein, the term "detectable label" is equivalent to the term "label". Indication that a label is "directly detectable" means that the label is directly involved in signal generation (e.g., a fluorophore or a moiety having characteristic light absorbing, reflecting, or scattering properties, or a radioactive moiety). In contrast, an "indirectly detectable" label requires the presence of at least one additional substance for a detectable signal to be generated. Examples of indirectly detectable labels include an enzyme which reacts with a substrate to produce a colored, fluorescent, or chemiluminescent species, and a specific binding moiety which specifically binds with the other of a specific binding pair thereby associating a signal generating substance or moiety with the indirect label.

The term "full-coated label" refers to a construct, often a particle, which bears or includes detectable moieties and which is either a layered label as defined below or has at least one protein coating which is substantially fully linked to the surface below (i.e., a "fully linked coating label"), e.g., to the particle surface. In most cases, the protein will be fully linked through amines, e.g., such that accessible amines are substantially depleted. In most cases, such a full-coated label has one or more coatings which essentially fully cover the coated particle or interior portions of a layered construct which does not have a solid phase particle core.

The term "layered label" refers to a construct, usually a particle, which bears or includes detectable moieties and which has at least two layers of a polymer material or materials. In many cases, there are covalent links between the layers. In most cases, the layers will be hydrophilic. The layered label may have a core particle, e.g., a polystyrene particle, or may be formed without a core. The detectable moieties may, for example, be covered by the layers, and/or may be distributed in or between layers. For layered labels having a core particle and detectable moieties covered by the layers, detectable moieties may be embedded in the core particles and/or on the surface of the core particles.

The term "staged label" refers to a construct, often a particle, which is protein coated with covalently linked protein. The protein is attached in a manner which essentially depletes functional groups of at least one type in the protein. Additional functional groups are then created in the protein, e.g., by reduction of disulfide bonds. Such constructs, e.g., particles, bear or include detectable moieties. The protein coating has one or more additional moieties linked through —SH groups resulting from reduction of the disulfide bonds or through functional groups derived from such reduced disulfide bonds. Such additional moieties may be of various types, for example, members of specific binding pairs (e.g., antigen for an antigen-antibody pair, or biotin for a streptavidin pair), detectable moieties, or additional coating species, which may be of the same or different protein or of a different type, e.g., a polysaccharide or synthetic polymer.

With respect to the present assays, the term "homogeneous assay" refers to an assay conducted in such manner that signal from label linked with analyte is detected in the presence of unlinked analyte label. In many cases, the assay is conducted without any separations, i.e., from addition of sample to signal reading. The term "heterogeneous assay" refers to an assay conducted in such manner that signal from label linked with analyte is detected after removal of analyte label from the vicinity of the label linked with analyte. In many cases, the analyte with linked label is immobilized, e.g., by binding with antibody linked with a solid phase substrate) and unlinked label is washed away or otherwise removed.

The terms "lateral flow assay" and "strip assay" are used herein equivalently to refer to assay formats, usually immunoassays, in which the test sample flows along a solid phase substrate (usually a membrane such as nitrocellulose, which may be adhered to a backing material impervious to the liquid used in the assay) via capillary action from a sample application zone into a fluid sink. The sample commonly encounters a detection reagent (commonly dried in a reagent pad downstream of the sample application zone; commonly a colored reagent) which mixes with the sample and transits the solid phase substrate encountering one or more lines or zones which have been pretreated with an appropriate specific binding moiety (typically an antibody or antigen). Depending upon the analytes present in the sample, the detection reagent can become bound at the test line or zone. After passing over the detection lines or zones, the fluid goes into a fluid sink (commonly an absorbent material).

The term "analyte" is used herein in the usual manner for in vitro biological assays, referring to a substance, e.g., an ion, molecule, or complex, which is detected and/or quantitated or at least intended to be detected and/or quantitated in an assay.

As used herein, the term "analyte-specific binding reagent" and "analyte-binding agent" and "specific binding agent" refer to a molecule or complex that specifically binds to desired analyte, and may also include moieties having other functions, such as labeling the molecule or complex. In some, but not all embodiments, the analyte-binding agent undergoes a detectable structural change upon binding analyte (e.g., an allosteric structural change). Examples include antibodies (including antibody fragments and other derivatives), aptamers, molecularly imprinted polymers, specific binding polypeptides, and specific binding small molecules (e.g., boronic acid derivative, such as phenylboronic acid, for Hb A1c).

The term "antibody" is used herein in the broadest sense and is intended to include intact monoclonal antibodies and polyclonal antibodies, as well as derivatives, variants, fragments and/or any other modification thereof so long as they exhibit the desired binding activity. Antibodies encompass immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and $Fab_2$ fragments, and a Fab expression library. Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Antibodies may be derived from a variety of sources, e.g., human, goat, mouse, rabbit, rat, sheep, camellid, and shark among others. Also included are chimeric antibodies, for example, monoclonal antibodies or modifications thereof that are specific to more than one source, e.g., a mouse or human sequence. Further included are camelid antibodies or nanobodies. Antibodies also include multi-specific, e.g., bispecific (e.g., multivalent, or multimeric) antibodies and functional fragments thereof. It will be understood that each reference to "antibodies" or any like term, herein includes intact antibodies, as well as any modifications thereof.

As used in connection with the present invention, the terms "glycation" and "glycated" and the like refer to non-enzymatic attachment of a glucose moiety.

Reference to a "fraction of glycated protein in a sample" and like terms means, for a particular identified protein, the ratio of the level of glycated protein to the level of total protein, or alternatively ratio of glycated protein to un-glycated protein. The ratio may be expressed in various ways, e.g., as conventional fraction, decimal fraction, or as percentage.

In connection with the present assays, the term "total protein" refers to the level of a particular protein, and not to the combined level of all proteins in a sample or in an organism(s) from which a sample is taken.

Indication that a protein or peptide is "susceptible to glycation" means that the protein or peptide contains at least one site or residue which can be glycated in vivo under conditions of high blood glucose. Non-limiting examples of such glycation sites are the N-terminal amino acids of hemoglobin and serum albumin.

Reference is made herein to an "unglycated version" of a protein or peptide and to a "glycated version" of the protein or peptide. A "glycated version" means a particular protein or peptide which is glycated, while "un-glycated version" refers to the same protein or peptide which is not glycated, or at least is not glycated at a site to be detected in the relevant assay.

As used herein, the term "fast reconstituting reagent pellet" refers to a dry reagent pellet which reconstitutes rapidly upon contact with assay solution, usually within 5, 3, 2, 1, 0.5, 0.3, 0.2, or even 0.1 seconds following contact with reagent solution under normal room temperature assay conditions. In this context, depending on the stage in the assay, assay solution can refer to, for example, blood sample, lysed blood sample, A1c-containing standard sample solution, sample solution containing magnetic beads, sample solution containing magnetic beads bound with hemoglobin, sample solution containing magnetic beads and labeled anti-A1c, and the like. Fast reconstituting reagent pellets useful in this invention include, for example, pellets containing RBC-lysing agents(s) as the principal active agent, pellets containing anti-Hb beads or other particles (which may be labeled) as the principal active agent, pellets containing anti-A1c and/or detectable label which is linked or links with the anti-A1c as the principal active agent. Such principal agent agents may also be combined with two or more such active agents (e.g., anti-Hb particles and anti-A1c) in a single pellet. Commonly, the reagent pellet will also contain one or more buffering agents. Fast reconstituting reagent pellets useful in this invention are described in U.S. patent application Ser. No. 14/106,930, now abandoned, which is incorporated herein by reference in its entirety, including for its description of fast reconstituting reagent pellets and their preparation.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to the particular labels used. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values or value range endpoints are provided for embodiments, additional embodiments are described by taking any 2 different values as the endpoints of a range or by taking two different range endpoints from specified ranges as the endpoints of an additional range. Such ranges are also within the scope of the described invention. Further, specification of a numerical range including values greater than one includes specific description of each integer value within that range.

Thus, additional embodiments are within the scope of the invention and within the following claims.

What is claimed is:

1. A method for determining a fraction of glycated hemoglobin in a sample, comprising
contacting a surface bearing a first binding agent specific for total hemoglobin with
a) a sample containing total hemoglobin in sufficient volume whereby binding of total hemoglobin on the surface is saturated; and
b) a second binding agent comprising an antibody that is specific for an epitope on hemoglobin A1c at the N-terminus of the hemoglobin A1c beta chain and labeled with a label; and
detecting at least one signal from the label,
wherein the first binding agent comprises an antibody that binds within hemoglobin beta chain amino acids 3-20 or 7-25;
wherein binding of the first binding agent with the hemoglobin causes exposure of the amino terminus of the beta chain of bound hemoglobin;
wherein the second binding agent preferentially binds with hemoglobin A1c bound with the first binding agent over binding with unbound hemoglobin A1c; and
wherein a level of the at least one signal is indicative of a fraction of hemoglobin A1c relative to total hemoglobin.

2. The method of claim 1, wherein the surface is a magnetic particle.

3. The method of claim 1, wherein the first binding agent binds within beta chain amino acids 7-25.

4. A method for determining a fraction of Hb A1c in a sample containing hemoglobin, comprising
contacting magnetic beads comprising a first label and linked with a first binding agent which is an antibody that binds within beta chain amino acids 3-20 or 7-25 of hemoglobin, wherein binding of the first binding agent with the hemoglobin causes exposure of the amino terminus of the beta chain of bound hemoglobin, with a) a sample comprising total hemoglobin in sufficient volume and concentration whereby binding of total hemoglobin on the labeled magnetic beads is saturated; and
b) a second binding agent specific for an Hb A1c subpopulation of the total hemoglobin and labeled with a second label, wherein the second binding agent binds the N-terminus of the Hb A1c beta chain, and wherein the second binding agent preferentially binds with hemoglobin A1c bound with the first binding agent over binding with unbound hemoglobin A1c;
thereby forming sandwich complexes comprising the labeled magnetic beads with the bound total hemoglobin, and the second binding agent bound to the Hb A1c subpopulation,
separating unbound second binding agent from the second binding agent in the sandwich complexes,
detecting a second signal from the second label in the sandwich complexes, wherein a level of the second signal is indicative of an amount of Hb A1c in the sample, and
detecting a first signal from the labeled magnetic beads, wherein a level of the first signal is indicative of a number of the labeled magnetic beads and therefore indicative of an amount of total hemoglobin in the sample,
wherein the amount of Hb A1c compared to the amount of total hemoglobin indicates a fraction of total hemoglobin in the sample which is glycated hemoglobin.

5. The method of claim 4, wherein the first binding agent binds within beta chain amino acids 7-25.

6. The method of claim 4, wherein the method further comprises detecting hemoglobin S, C, E or D.

7. A method for one-step measurement of a fraction of glycated hemoglobin in a sample, comprising
(a) lysing a blood sample;
(b) contacting the lysed blood sample with a predefined quantity of solid phase media modified with antibody binding total hemoglobin thereby saturation binding total hemoglobin to the solid phase media, wherein the antibody binds hemoglobin beta chain within amino acids 7-25, wherein binding of the antibody with the hemoglobin causes exposure of the amino terminus of the beta chain of bound hemoglobin;

(c) contacting hemoglobin bound on the solid phase media with a reagent that specifically binds the N-terminus of the beta chain of hemoglobin A1c; wherein the reagent preferentially binds with hemoglobin A1c bound with the antibody over binding with unbound hemoglobin A1c; and (d) determining a level of the reagent specifically bound to hemoglobin A1c as an indication of a fraction of bound total hemoglobin which is glycated.

8. The method of claim 7, wherein the solid phase media is particles or planar surface.

9. The method of claim 7, wherein the reagent is an antibody, an aptamer, a molecularly imprinted polymer, a polypeptide, or a boronic acid derivative.

10. The method of claim 7, wherein the reagent is labeled with a detectable label and the method further comprises detecting a signal from the label.

11. The method of claim 10, wherein the label is a time resolved fluorescent (TRF) label.

12. The method of claim 7, wherein the reagent is not labeled with a detectable label, and the method further comprises contacting reagent bound to hemoglobin A1c bound on the solid phase media with labeled second reagent linked with a detectable label.

13. The method of claim 12, wherein the method further comprises detecting signal from the detectable label.

14. The method of claim 12, wherein the hemoglobin beta chain in the blood sample is not denatured.

15. The method of claim 7, wherein the method is performed as a homogeneous assay.

* * * * *

SEQUENCE LISTING

```
<160> NUMBER OF SEQ ID NOS: 1

<210> SEQ ID NO 1
<211> LENGTH: 146
<212> TYPE: PRT
<213> ORGANISM: Homo sapiens
<220> FEATURE:
<221> NAME/KEY: PEPTIDE
<222> LOCATION: (1)..(146)
<223> OTHER INFORMATION: Subject to acetylation at position 1.
<300> PUBLICATION INFORMATION:
<308> DATABASE ACCESSION NUMBER: UniProt/P68871
<309> DATABASE ENTRY DATE: 2007-01-23
<313> RELEVANT RESIDUES IN SEQ ID NO: (2)..(147)
```

```
<400> SEQUENCE: 1

Val His Leu Thr Pro Glu Glu Lys Ser Ala Val Thr Ala Leu Trp Gly
1               5                  10                  15

Lys Val Asn Val Asp Glu Val Gly Gly Glu Ala Leu Gly Arg Leu Leu
                20                  25                  30

Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145
```